(12) United States Patent
Gebhardt

(10) Patent No.: US 9,540,648 B2
(45) Date of Patent: Jan. 10, 2017

(54) THERAPEUTIC USE OF ACTIVATORS OF ZINC FINGER PROTEIN GL13

(71) Applicant: Universität Leipzig, Leipzig (DE)

(72) Inventor: Rolf Gebhardt, Leipzig (DE)

(73) Assignee: Universität Leipzig, Leipzig (DE)

( * ) Notice: Subject to any disclaimer, the term of this patent is extended or adjusted under 35 U.S.C. 154(b) by 0 days.

(21) Appl. No.: 14/374,887

(22) PCT Filed: Jan. 25, 2013

(86) PCT No.: PCT/EP2013/051425
§ 371 (c)(1),
(2) Date: Jul. 25, 2014

(87) PCT Pub. No.: WO2013/110749
PCT Pub. Date: Aug. 1, 2013

(65) Prior Publication Data
US 2014/0336111 A1   Nov. 13, 2014

(30) Foreign Application Priority Data

Jan. 26, 2012 (GB) .................................. 1201298.5

(51) Int. Cl.
| | |
|---|---|
| A61K 38/22 | (2006.01) |
| A61K 31/4436 | (2006.01) |
| A61K 31/381 | (2006.01) |
| A61K 38/17 | (2006.01) |
| A61P 1/16 | (2006.01) |
| C12N 15/113 | (2010.01) |
| A61K 45/06 | (2006.01) |
| C07K 14/575 | (2006.01) |

(52) U.S. Cl.
CPC ............ *C12N 15/1136* (2013.01); *A23L 33/13* (2016.08); *A61K 31/381* (2013.01); *A61K 31/4436* (2013.01); *A61K 38/1709* (2013.01); *A61K 38/22* (2013.01); *A61K 38/2264* (2013.01); *A61K 45/06* (2013.01); *C12N 15/1135* (2013.01); *C12N 15/1138* (2013.01); *A23V 2002/00* (2013.01); *C12N 2310/11* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 6,291,516 B1 | 9/2001 | Dudek et al. | |
| 6,613,798 B1 | 9/2003 | Porter et al. | |
| 6,683,108 B1 | 1/2004 | Baxter et al. | |
| 6,683,192 B2 | 1/2004 | Baxter et al. | |
| 6,686,388 B2 | 2/2004 | Dudek et al. | |
| 7,115,653 B2 | 10/2006 | Baxter et al. | |
| 8,129,425 B2 | 3/2012 | Baxter et al. | |
| 8,501,686 B2 | 8/2013 | Oral et al. | |
| 8,852,937 B2 | 10/2014 | Baxter et al. | |
| 2005/0070578 A1 | 3/2005 | Baxter et al. | |
| 2006/0078499 A1 | 4/2006 | Hen et al. | |

FOREIGN PATENT DOCUMENTS

| | | |
|---|---|---|
| WO | 2009/149379 | 12/2009 |
| WO | 2011/109711 | 9/2011 |

OTHER PUBLICATIONS

Martin et al, 2002. Drug Development Research. 57: 107-114.*
Cousin et al (2007. Biochimie. 89: 1447-1453).*
Domvri et al, 2012. Current Gene Therapy. 12: 463-483.*
Vidal et al. 2005. European Journal of Cancer. 41: 2812-2818.*
Pirollo et al, 2008. Cancer Res. 68(5): 1247-1250.*
Carney, Tom J. et al., "Drugging Hedgehog: signaling the pathway to translation," BMC Biology 11:37(2013).
Stanton, Benjamin Z. et al., "Small-molecule modulators of the Sonic Hedgehog signaling pathway," Mo. BioSyst. 6 (2010).
Brunton, S.A. et al., "Potent Agonists of the Hedgehog Signaling Pathway," Bioorg Med Chem Lett 19:4308-11 (2009).
Choi, S.S. et al., "T1960 Leptin Activates Hedgehog Pathway Signaling and Promotes Myofibroblastic Transition and Accumulation in Rat Hepatic Stellate Cells," Gastroenterology 138(5):S-837 (2010).
Javor, E.D. et al., "Leptin Reverses Nonalcoholic Steatohepatitis in Patients With Severe Lipodystrophy," Hepatology 41(4):753-60 (2005).
Greenbaum, L.E., "Hedgehog Signaling in Biliary Fibrosis," J Clin Invest 118(10):3263-5 (2008).
Matz, M. et al., "Der Hedgehog Signalweg als neuer Master-Regulator des Lipidmetabolismus in Hepatocyten: Implikationen fur die hepatische Steatose," Z Gastroenterology 49:V2_02 (2011).
Omenetti, A. et al., "The Adventures of Sonic Hedgehog in Development and Repair. II. Sonic hedgehog and liver development, inflammation, and cancer," Am J Physiol Gastrointest Liver Physiol 294:G595-98 (2008).
Omenetti, A. et al., "Repair-Related Activation of Hedgehog Signaling Promotes Cholangiocyte Chemokine Production," Hepatology 50(2):518-27 (2009).
Sicklick, J.K. et al., "Role for Hedgehog signaling in hepatic stellate cell activation and viability," Laboratory Investigation 85:1368-80 (2005).
Sicklick, J.K. et al., "Hedgehog signaling maintains resident hepatic progenitors throughout life," Am J Physiol Gastrointest Liver Physiol 290:G859-70 (2006).

(Continued)

*Primary Examiner* — Zachary Howard
(74) *Attorney, Agent, or Firm* — Mastermind IP Law P.C.; Diane L. Gardner

(57) ABSTRACT

The present invention relates to the therapeutic use of activators of the zinc finger protein GLI3 in diseases that are associated with reduced Hedgehog signaling in hepatocytes, in particular Polycystic ovary syndrome, Steatosis hepatis, Steatohepatitis and/or Adipositas. The invention further relates to methods of treating an individual with said activator, a pharmaceutical composition comprising said activator and the use of said activator as food supplement.

9 Claims, 18 Drawing Sheets

(56) References Cited

OTHER PUBLICATIONS

Syn, W. et al., "Hedgehog-Mediated Epithelial-to-Mesenchymal Transition and Fibrogenic Repair in Nonalcoholic Fatty Liver Disease," Gastroenterology 137:1478-88 (2009).
Matz-Soja, M. et al., "Hedgehog Signaling is a Potent Regulator of Liver Lipid Metabolism and Reveals a GLI-Code Associated with Steatosis," eLife 2016; 5:e13308.
Suh, J.M. et al., "Hedgehog Signaling Plays a Conserved Role in Inhibiting Fat Formation," Cell Metabolism 2006; 3:25-34.
Dellovade, T. et al., "The Hedgehog Pathway and Neurological Disorders," Annu. Rev. Neurosci. 2006; 29:539-63.
Altman, D. et al., "Second Medical Use or Indication Claims," AIPPI Question Q238 2014; pp. 1-12.

\* cited by examiner a)

b)

c) d)

a)

b)

a)

b)

c)

d)

a)  b)

a) Smo$^{+/+}$ b) Smo -/- c) Smo$^{+/+}$ d) Smo -/-

THERAPEUTIC USE OF ACTIVATORS OF ZINC FINGER PROTEIN GLI3

PRIORITY

This application claims priority to International Application Serial No. PCT/EP2013/051425 filed on Jan. 25, 2013, which claims priority to Application Serial No. GB1201298.5 filed on Jan. 26, 2012, the contents of which are incorporated in their entirety by reference herein.

FIELD OF THE INVENTION

The present invention relates to the therapeutic use of activators of the zinc finger protein GLI3 in diseases that are associated with reduced Hedgehog signaling in hepatocytes, in particular Steatosis hepatis, Steatohepatitis, adiposity and/or Polycystic ovary syndrome. The invention further relates to methods of treating an individual with said activator, a pharmaceutical composition comprising said activator and the use of said activator as food supplement.

BACKGROUND OF THE INVENTION

The hedgehog signaling pathway is a key regulator in embryonic development. The pathway includes the intercellular signaling molecule "Hedgehog" (Hh) that was first identified in *Drosophila*, where Hh is involved in establishing the basis of the fly body plan. In mammals three Hedgehog homologues exist, Sonic hedgehog (Shh), Indian hedgehog (Ihh) and Desert hedgehog (Dhh). Shh signaling is the best studied mechanism and is crucial during vertebrate embryonic development. Shh is known to bind on the Patched-1 (Ptch1) receptor on its target cell. In the absence of Shh, Ptch1 inhibits the protein Smoothened (Smo) by transporting a small molecule inhibitor of Smo, probably vitamin D or a related precursor. When Smo is inhibited, two members of the transcription factors of the GLI family, namely GLI2 and GLI3 are truncated to their repressor forms, while GLI1 is completely degraded. The truncation of GLI2 and GLI3 is initiated by a complex of proteins including Supressor of fused (SuFu). Upon Shh binding, the transport activity of Ptch1 is switched from the Smo inhibitor to oxysterols, thereby allowing oxysterols to accumulate around Smo. Thus, Smo is activated leading to an activation cascade for all three members of the GLI family which then exist in their untruncated, activating form. The activated GLI molecules accumulate in the nucleus and control transcription of hedgehog target genes.

Disrupted hedgehog signaling in embryonic development leads to severe developmental abnormalities, particularly in the brain, skeleton, musculature, gastrointestinal tract and lungs. Strongly activated hedgehog signaling has been described in cancers of various organs, like brain, lung, mammary gland, prostate and skin.

Several activators of Hh signaling have been described. Brunton 2009 discloses Hh-agonists according to following formula (1)

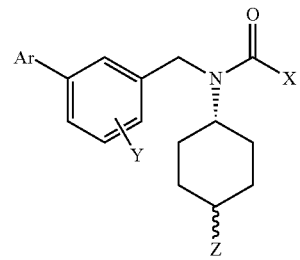

Apart from being involved in embryonic development and cancer development it is suggested that Hh signaling in different cells is involved in the development of a variety of diseases. It is described that Hh signaling regulates epithelial-mesenchymal transition in cholangiocytes of the adult bile duct during biliary fibrosis (Omenetti 2009, Greenbaum 2008). Further, activation of Hh signaling has been described to be therapeutically useful in the treatment of depression (US2006078499A1). Activators of Hh signalling were described for therapeutic application to epithelial tissues. Here, treatment of tissue disorders as well as surgical or cosmetic applications of tissues like skin, cornea, lens and other ocular tissue, mucosal membranes and periodontal epithelium should be mentioned (U.S. Pat. No. 7,115,653, WO 0174344 A2, EP 1671634 A1).

The role of hedgehog signaling in liver cells recently got into focus of research. Sicklick 2005 and Sicklick 2006 proposed that Hh signaling is required for the activation of hepatic stellate cells (HSC) and that Hh signaling is relevant for the survival of hepatic precursor cells (HPC). The review article by Omenetti 2008 summarizes the role of Hh signaling during liver development, inflammation and cancer. According to Omenetti 2008, the role of Hh signaling in liver development is not fully understood, whereas in the adult liver the expression of Hh ligands as well as a responsiveness to Hh ligands was observed in HSC and liver epithelial progenitors. Constitutive activation of Hh signalling has been observed in both hepatocellular carcinoma and cholangiocarcinoma. According to Omenetti 2008, it is believed that mature hepatocytes are not Hh-responsive.

The role of Hh signalling in non-alcoholic fatty liver disease (NAFLD) was examined in several studies. Syn 2009 studied Hh signaling in the pathogenesis of NAFLD, non-alcoholic steatohepatitis (NASH) and cirrhosis of the liver. Syn 2009 observed low expression of Shh and GLI2 in NAFLD-patients and increased expression thereof in NASH and cirrhosis. In summary, it is suggested that activation of Hh signaling in HPC is associated with disease pathogenicity.

Trappoliere 2005 give an overview on strategies for treatment of fatty liver diseases. Current methods of treatment include
- treating the underlying cause or predisposition (weight, metabolism disorders, diabetes),
- modulation of cytokine levels involved in the disease,
- inhibition of lipid peroxidation and progression of fibrosis (e. g. by administration of antioxidants or antifibrotic substances).

OBJECTIVE OF THE INVENTION

It is the object of the invention to provide medicaments for the treatment of diseases associated with an imbalanced liver lipid metabolism and/or with increased fat deposits, such as fatty liver diseases, adiposity or polycystic ovary syndrome (PCOS).

DESCRIPTION OF THE INVENTION

The object is solved by providing an activator of the zinc finger protein GLI3 for use in the treatment of a disease associated with an imbalanced liver lipid metabolism and/or with increased fat deposits, preferably for the treatment of an aforementioned disease associated with reduced Hedgehog signaling in hepatocytes.

Another aspect of the invention is the use of an activator of the zinc finger protein GLI3 for activating hedgehog signaling in hepatocytes, preferably for the treatment of a disease associated with reduced Hedgehog signaling in hepatocytes.

The invention is based on the surprising observation that moderate Hh signaling in adult hepatocytes is required for normal liver function and that disruption of or down-regulation of Hh signaling via Smo in hepatocytes results in an increased expression of lipogenic transcription factors and in the development of symptoms of Steatosis hepatis, adiposity and Polycystic ovary syndrome (PCOS). These observations were not expected, as the prior art discloses that adult hepatocytes are not Hh-responsive.

In experiments performed with a mouse model comprising an inducible knock-out of Smo in hepatocytes, the inventors observed massive Steatosis hepatis about 3 to 5 weeks after disruption of Hh signaling. It was observed that deletion or inhibition of Smo-signaling resulted in a selective down-regulation of GLI3 which is associated with an induction of lipogenic transcription factors. Massive visceral fat deposits were observed in the affected animals that were associated with increased serum levels of dihydroepiandrosteron (DHEA). Female mice with conditional Smo knock-out in hepatocytes were infertile with symptoms similar to PCOS. Based on these observations the inventors developed a therapeutic concept to treat diseases that are associated with reduced Hh signaling in hepatocytes by administering an activator of GLI3.

In one aspect of the invention the disease treated with an activator of GLI3 is a fatty liver disease, preferably non-alcoholic fatty liver disease (NAFLD), preferably non-alcoholic Steatosis hepatis or non-alcoholic Steatohepatitis (NASH).

In a further aspect of the invention the disease treated with an activator of GLI3 is adiposity. In this aspect the activator of GLI3 is preferably used for reducing visceral fat deposition or for prevention of visceral fat deposition.

In a further aspect of the invention the disease treated with an activator of GLI3 is Polycystic ovary syndrome (PCOS).

The development of the aforementioned different diseases involves a reduced Hh signaling in hepatocytes. In a preferred aspect of the invention the activator of GLI3 is administered to hepatocytes. By this, side effects caused by hedgehog activation in other cells than hepatocytes are minimized.

An activator of GLI3 within the meaning for this invention includes all molecules that upon administration to an individual induce activation and/or increased expression of GLI3. By this, upstream activators as well as direct activators of the GLI3 molecule are explicitly included in the definition of a "GLI3 activator". In one aspect of the invention the activator of GLI3 is selected from
 activators of the hedgehog signaling pathway,
 inhibitors of suppressors of the hedgehog signaling pathway,
 leptin or
 inhibitors of suppressors of zinc finger protein GLI3 (preferably selected from substances inhibiting hepatocyte growth factor (HGF)).

The term "activators of the hedgehog signaling pathway" (herein also referred to as "hedgehog agonist") means agents that upon administration lead to activation of the transcription of hedgehog target genes. Preferred activators of the hedgehog signaling pathway are selected from hedgehog ligands, activators of Smoothened (Smo) and inhibitors of the interaction between Patched (Ptch-1 and/or Ptch-2) and Smo (resulting in Smo inhibition). Particularly preferred activators of Hh signaling are selected from the proteins Sonic hedgehog (Shh), Indian Hedgehog (Ihh), Desert hedgehog (Dhh) and Smoothened agonist (SAG). A particularly preferred activator of GLI3 is SAG.

Preferred inhibitors of suppressors of the hedgehog signaling pathway are selected from inhibitors of Sufu, Patched-1 or Patched-2.

One direct activator of GLI3 is leptin. In a particularly preferred aspect of the invention, leptin is only used in combination with at least one further activator of GLI3.

Preferred inhibitors of suppressors of GLI3 are selected from substances inhibiting hepatocyte growth factor (HGF).

Activators of GLI3 as used according to the invention are preferably selected from proteins, lipids, oxysterols, small molecules or nucleic acids. Preferred nucleic acids are antisense oligonucleotides (preferably with a length of 15-50 nucleic acids) or small interfering RNA (siRNA) or small hairpin RNA (shRNA) (both siRNA and shRNA preferably with a length of 19-30 bp).

Antisense oligonucleotides as used according to the invention are single strands of DNA or RNA that are complementary to a nucleic acid sequence (DNA or RNA) in order to inhibit expression of a gene or translation of RNA. The term "antisense oligonucleotides" includes DNA or RNA polymers and other linear polymers comprising the bases adenine, cytosine, thymine and guanine and/or other, optionally modified, nucleobases. Antisense oligonucleotides include nucleotides with a modified backbone or modified 3' or 5' terminus. Preferred modifications are backbone modifications with phosphothioate, phosphoramidite or O-methyl-derivatization, peptide nucleic acids (PNA), locked nucleic acids (LNA), morpholino oligonucleotides, or mixed-backbone oligonucleotides.

Oxysterols as used according to the invention are oxidized derivatives of cholesterol. Preferred oxysterols are osteoinductive oxysterols, preferably 20(S)-hydroxycholesterol, 22(S)-hydroxycholesterol.

The term "small molecule" refers to a compound having a molecular weight of less than 2500 Dalton (Da), preferably less than 2000 Da.

In a preferred aspect of the invention the activator of GLI3 is siRNA or shRNA (preferably siRNA) that inhibits expression of suppressors of the hedgehog signaling pathway or direct suppressors of GLI3. Preferred siRNA or shRNA used according to this aspect of the invention inhibits expression of Sufu, Patched-1, Patched-2 or HGF; particularly preferred Sufu. Preferred GLI3 activating siRNA comprises a nucleic acid sequence according to the following sequences, which represents double stranded siRNA inhibiting Sufu:

SEQ ID No. 7
CCCUUGGACUAUGUUAGCAUGUACA,

SEQ ID No. 8
UGUACAUGCUAACAUAGUCCAAGGG.

Preferably antisense oligonucleotides, siRNA or shRNA as used according to the invention comprise a nucleic acid sequence that is complementary to a partial sequence of the gene to be inhibited. Therefore, preferred antisense oligonucleotides, siRNA or shRNA comprise a nucleic acid sequence that is complementary to a part of the nucleic sequence of Sufu, Patched-1, Patched-2 or HGF; particularly preferred Sufu.

Preferred activators of GLI3 as used according to the invention are agents activating hedgehog signaling that are disclosed in Brunton 2009, U.S. Pat. No. 7,115,653, WO 01074344 A2, WO 2000041545 A2, WO 03027234 A2, US 2006078499 A1 and EP 1671634 A1, all of which are fully incorporated herein by reference.

Preferred compounds disclosed by Brunton 2009 that are used according to the invention are compounds according to the following formula (1)

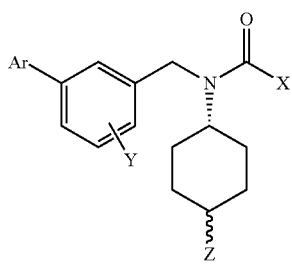
(1)

wherein X is selected from thiophenes or benzothiophenes, preferably 3-chlorobenzothiophenes, 3-flourobenzothiophenes or 3-methylbenzothiophenes, according to one of the following formulae:

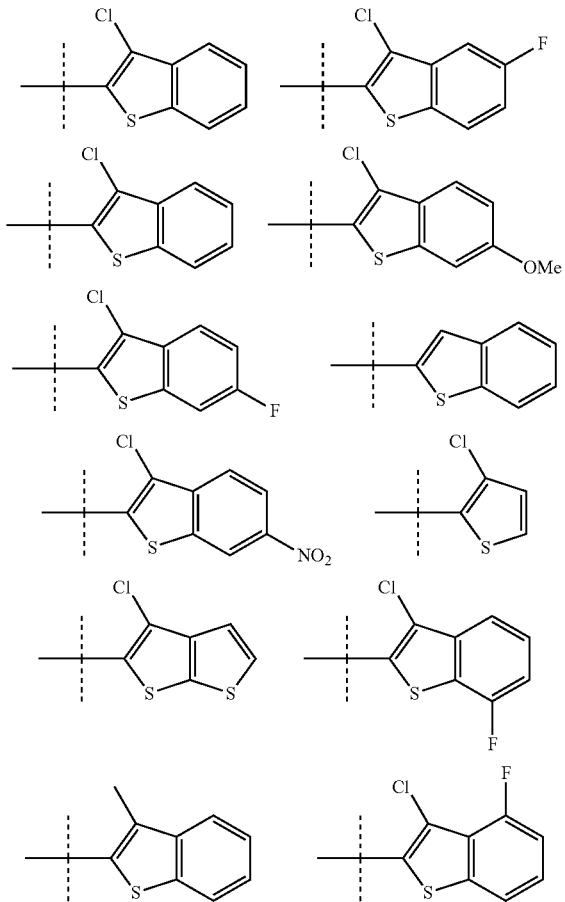

-continued

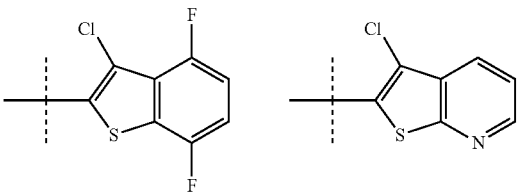

wherein Y is selected from 4- or 6-alkoxy (preferably methoxy), 4- or 6-alkyl (preferably methyl) or 4- or 6-halogen (preferably F);

wherein Z has the structure —$(CH_2)_n$—$NR_1R_2$, wherein $R_1$ and $R_2$ are selected from hydrogen and C1 to C10-alkyl, preferably wherein one of the rests $R_1$ and $R_2$ is C1 to C10-alkyl, preferably the C1 to C10-alkyl rest is selected from Methyl and Ethyl, and wherein n is selected from 0, 1 and 2, particularly preferred the rest Z is —NH-Et, —NH-Me, and —$CH_2$—NH-Me; and wherein Ar is selected from phenyl or substituted phenyl, preferably Ar is selected from one of the following formulae:

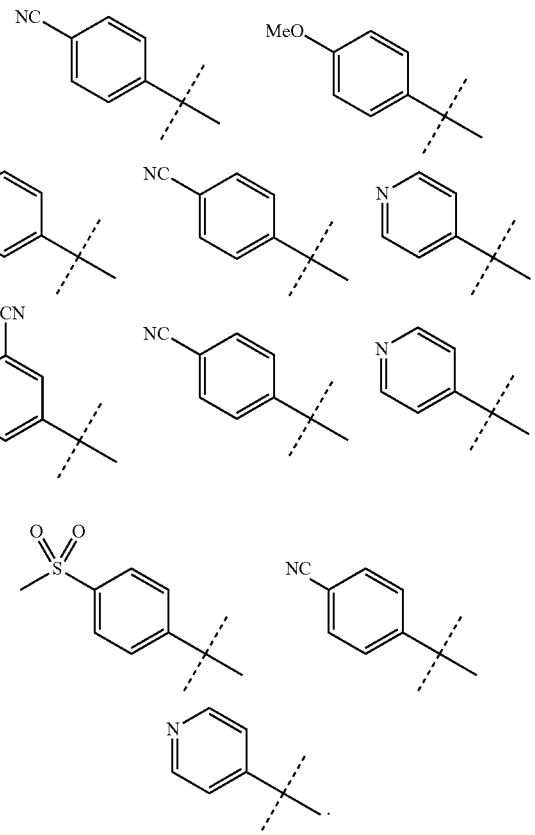

Preferably the compound according to formula (1) exhibits a structure according to formula (2) or (3), wherein in formula (2) R3 and R4 are independently from each other selected from H and F:

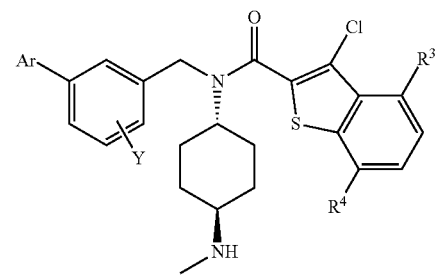

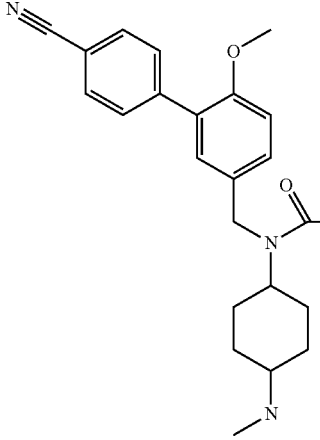

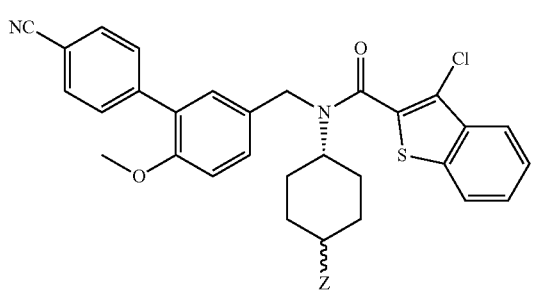

Particularly preferred compounds according to formula (1) are the following compounds (i) to (iv):

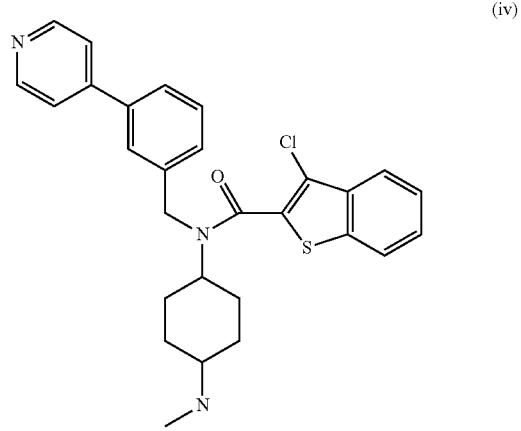

A particularly preferred activator of GLI3 is the following substance (21k)

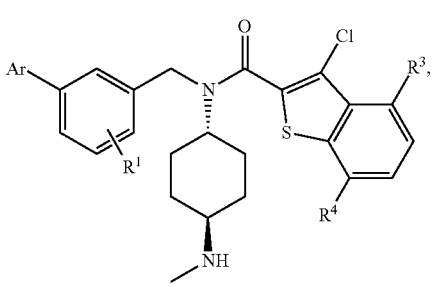

wherein Y=4-OMe, R$_3$=F, R$_4$=F and Ar=

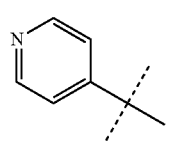

The therapeutic application of activators of GLI3 according to the invention can be performed by applying the activator of GLI3 alone or in combination with at least one further therapeutic agent, preferably a therapeutic agent that is known to be effective in the treatment of the disease to be treated with the activator of GLI3 (combinatory composition). Therefore, the invention is also directed to a pharmaceutical composition comprising at least one activator of the zinc finger protein GLI3, preferably as defined and preferred above, and at least one additional therapeutic agent, preferably a therapeutic agent for treatment of Steatosis hepatis or Steatohepatitis, preferably non-alcoholic fatty liver disease or non-alcoholic Steatohepatitis, adiposity (preferably for reducing visceral fat deposits), or PCOS in combination with a pharmaceutically acceptable carrier.

The pharmaceutical compositions according to the invention include various dosage forms and are preferred for oral, inhalational or parenteral, particularly preferably suitable for intravenous administration. Preferably, the parenteral pharmaceutical composition is in a form which is suitable for injection. Particularly preferred pharmaceutical compositions comprise a solution, emulsion or suspension of the activator of GLI3 in the pharmaceutically acceptable carrier.

Pharmaceutically acceptable carriers are preferably sterile liquids, especially water, buffered water, 0.4% saline, 0.3% glycine and the like. The pharmaceutical compositions may be sterilized by conventional, well known techniques. The compositions preferably contain pharmaceutically acceptable auxiliary substances, such as those that are required to assure physiological conditions and/or that increase the stability of the contained activator of GLI3 and the additional therapeutic agent. Preferred auxiliary substances are agents for adjusting the pH and buffering agents, preferably selected from sodium acetate, sodium chloride, potassium chloride, calcium chloride and sodium lactate.

The pharmaceutical composition according to the invention comprises a pharmaceutically effective amount of the activator of GLI3 and the at least one additional therapeutic agent.

Preferred additional therapeutic agents are selected from antidiabetic drugs and insulin sensitizers, preferably selected from biguanides (preferably metformin), agonists of the peroxisome-proliferator activated receptor-γ (preferably thiazolidinediones, in particular selected from pioglitazone, troglitazone and rosiglitazone), agonists of the peroxisome-proliferator activated receptor-δ (preferably GW501516), agonists of the glucagon-like peptide-1 receptor (preferably selected from exendin-4 and exenatide) and cannabinoid type I receptor blockers (preferably selected from rimonabanant, taranabant and otenabarant);

weight reducing drugs, preferably inhibitors of pancreatic lipase (preferably selected from tetrahydrolipstatin and lipstatin), lipid-lowering drugs, preferably statins and fibrates;

substances inhibiting the lipid peroxidation, preferably antioxidants (preferably selected from ascorbic acid, glutathione, melatonin, tocopherols and tocotrienols), polyunsaturated fatty acids, omega-3 fatty acids;

antifibrotic substances;

hepatoprotective agents, preferably selected from flavonolignans (preferably silibinin or silymarin);

anti-inflammatory agents.

The invention further comprises a method for treating a disease including the step of administering a therapeutically effective amount of an activator of the zinc finger protein GLI3, preferably as defined and preferred above, to an individual suffering from said disease. Preferred diseases to be treated are associated with reduced Hedgehog signaling in hepatocytes and include Steatosis hepatis or Steatohepatitis (preferably non-alcoholic fatty liver disease or non-alcoholic Steatohepatitis), adiposity, or PCOS. In one aspect of the invention the method of treatment includes administering the activator of GLI3 to hepatocytes of an individual. The method of treatment according to the invention can be effective for both human and animal subjects.

In one aspect the method of treatment according to the invention includes administering a pharmaceutical composition according to the invention to an individual suffering from said disease.

In another aspect the method of treatment according to invention includes administering an activator of GLI3 in form of a food supplement. Therefore, the invention also includes the use of an activator of GLI3 as food supplement. Food supplements comprising an activator of GLI3 can be administered prophylactically, preferably to individuals susceptible of developing a disease associated with reduced hedgehog signaling in hepatocytes as described above, or therapeutically for the treatment of said disease.

DESCRIPTION OF THE DRAWINGS

The invention is further illustrated by the following figures and examples without being limited to these.

EXAMPLE 1

Disruption of Hedgehog Signaling in Hepatocytes by Hepatocyte-Specific Ablation of Smoothened (Smo) Leads to Development of Steatosis Hepatis For studying the influence of hedgehog signaling on liver metabolism in adult mice a conditional hepatocyte-specific knock-out of Smoothened (Smo) was generated in a triple transgenic mouse model (herein referred to as "SLC-mice"). SLC-mice were generated by crossing double transgenic LC-1-Cre mice Smo$^{flox/flox}$ mice. When maintained in the absence of doxycycline, the transgenic SLC-mice developed without phenotype. Addition of 2 mg/ml doxycycline to the drinking water resulted in efficient and uniform loss of Smo in hepatocytes within less than 10 days (herein referred to as "SLC-KO mice" whereas mice that did not receive doxycycline are referred to as "SLC-WT mice").

Animal Care.

Mice were maintained in a pathogen-free facility in a 12:12 h LD cycle according to the German guidelines for the care and safe use of experimental animals. Animals had free access to regular chow (Sniff® M-Z V1124-0 composed of 22.0% protein, 50.1% carbohydrate, 4.5% fat; usable energy: 13.7 kJ/g; ssniff Spezialdiaten GmbH, Soest, Germany) and tap water throughout life. Before sacrifice (between 9 and 11 am), mice were starved for 24 h and re-fed with regular chow for 12 h, in order to obtain a synchronized feeding state.

Figure 1:
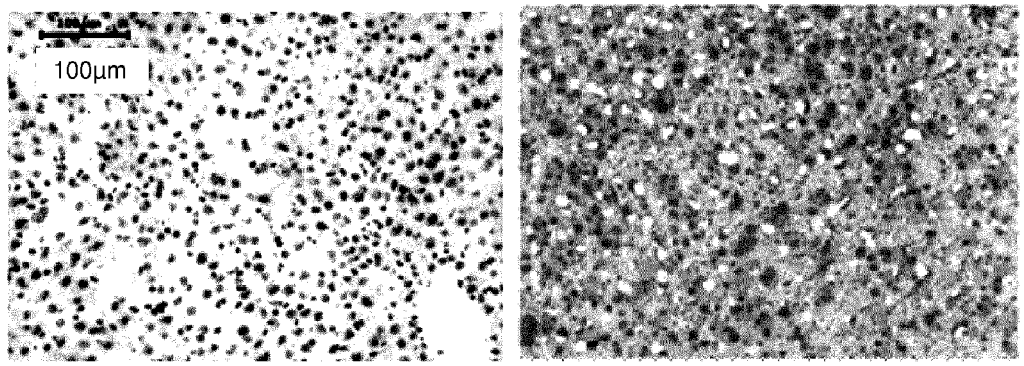
FIG. 1 Development of hepatic steatosis upon hepatocyte-specific ablation of Smoothened (Smo) in an inducible murine Smo$^{-/-}$ model. a) Oil red O staining image of liver sections from WT (left) and KO (right) SLC mice. b) Quantification of Oil red O stained area (n=7-10). c) and d) Cultured hepatocytes of c) WT and d) KO SLC mice stained with Oil red O.
Figure 1:
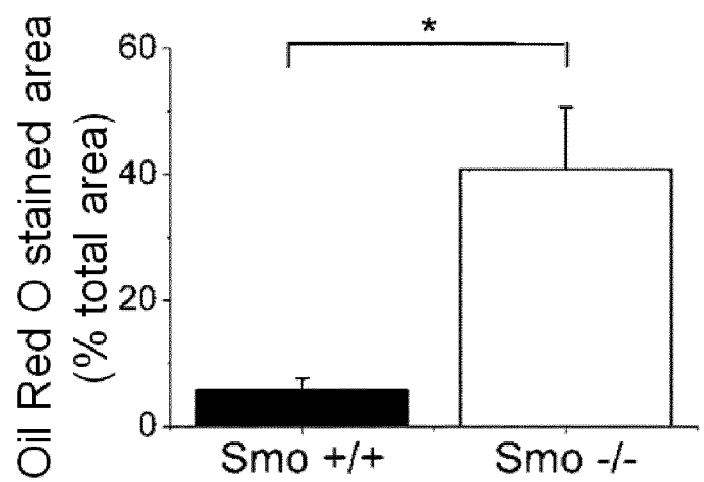
Figure 1:
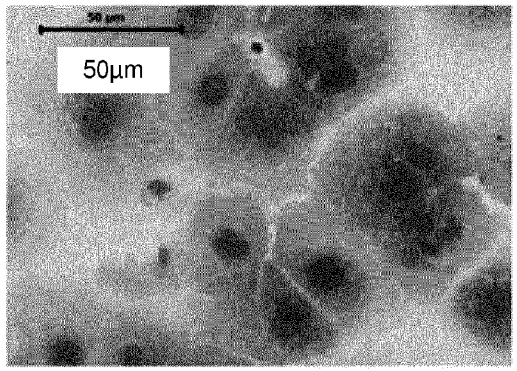
Figure 1:
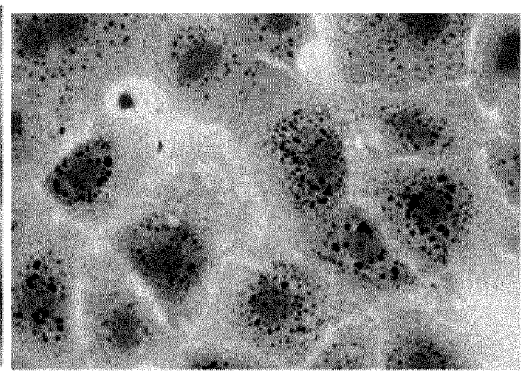

After induction of Smo knock-out at the age of 8 weeks (circumventing disturbance by hormonal changes during puberty) SLC-mice soon impressed by slower body weight gain and retarded growth which continued for at least 5 weeks. At sacrifice after this period the liver weight/body weight ratio was lower in male and female KO mice than in respective non-induced (WT) control mice (data not shown). Histological inspection of liver sections by Oil red O staining revealed pronounced steatosis upon ablation of Smo (FIGS. 1a and b).

Liver Sections.

Liver samples taken were shock-frozen and stored at −80° C. For quantitative and qualitative lipid analysis frozen sections were cut at 6 μm and stained with Oil red O as described before (Nunnari et al., 1989).

Oil Red O Quantification.

Oil red O staining of cryostat sections was assessed by bright-field microscopy. Digital images were taken from three contiguous microscopic fields per section covering the entire parenchyma between large vessels. Using UTHSCA Image Tool 3.0 software (University of Texas Health Science Center, San Antonio) the images were transformed to a binary format after appropriate thresholding. The same threshold was applied to all images from all sections. The area fraction, defined as (pixels over Oil red O)/(total pixels per image)×100, was determined for sections from n=10 and n=7 animals for SLC-WT and SLC-KO groups, respectively. Values are presented as area fraction percentage.

Cells from Smo KO mice (bottom row) show larger lipid droplets compared to WT hepatocytes (top row).

As demonstrated by staining with Oil red O hepatic steatosis in Smo knock-out mice was of the mixed macro- and microvesicular type (FIG. 1d). It was most prominent in the midzonal to periportal zone, but occasionally covered the entire parenchyma. In contrast, respective WT livers showed normal undisturbed parenchyma with rare, if any, microvesicular lipid droplets (FIG. 1c). Quantification of oil red O stained area revealed a 7-fold increase in SLC-KO mice (FIG. 1b). Inspection at earlier time points revealed the gradual aggravation of liver steatosis during the knockout-period starting 10 to 14 days after doxycycline.

Figure 11:
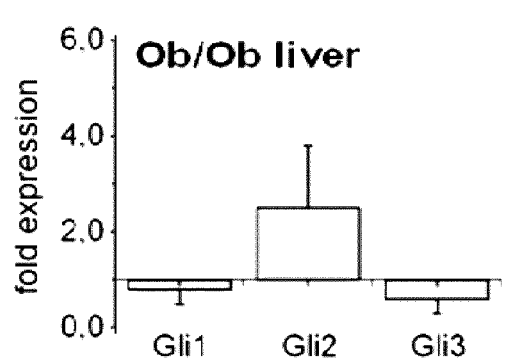
FIG. 11 GLI expression in a) murine model of hepatic steatosis (ob/ob mice) and b) in an inducible murine Smo$^{-/-}$ model five weeks after induction of Smo knock-out.
Figure 11:
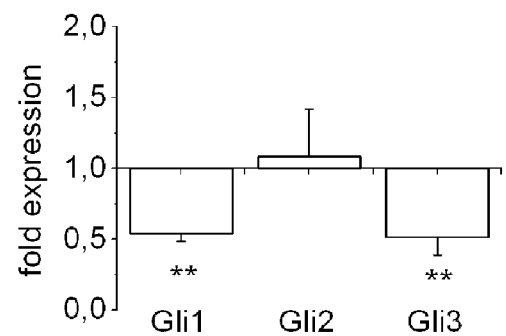

Gene expression of members of the GLI-family was analyzed in livers of WT and KO-SLC mice (FIG. 11b). A significant downregulation of GLI1 and GLI3 was observed that is in accordance with observations in livers from other murine models of hepatic steatosis, such as ob/ob mice (FIG. 11a).

The analyses were performed by quantitative Real time PCR as described in detail in Example 3 using the following primers:

TABLE 1

|  |  |  | SEQ ID No. |
|---|---|---|---|
| GLI1 | fw | cagggaagagagcagactgac | 19 |
|  | rev | cgctgctgcaagaggact | 20 |
| GLI2 | fw | actttctccacaccctgctg | 21 |
|  | rev | ggctgcgaggctaaagagtc | 22 |
| GLI3 | fw | ctggcttgattgttcacgag | 23 |
|  | rev | cagccctcatgctcacagac | 24 |

Figure 2:
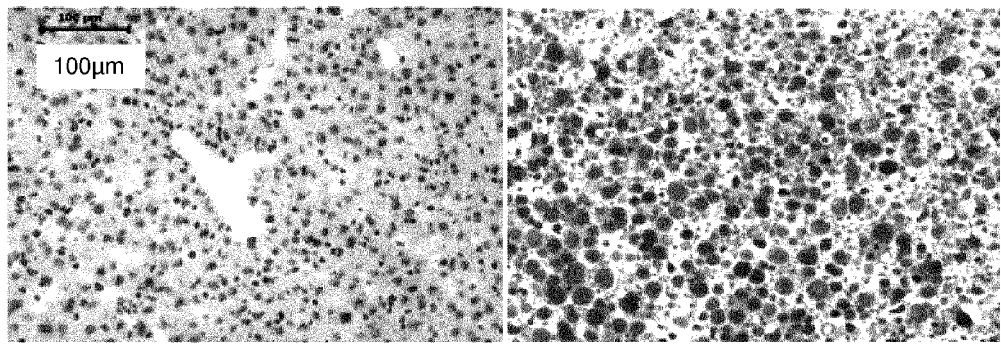
FIG. 2 Development of hepatic steatosis upon hepatocyte-specific ablation of Smoothened (Smo) in fetal stage. a) Oil red O staining image of liver sections from WT (left) and KO (right) SAC mice. b) Quantification of Oil red O stained area (n=5-7).
Figure 2:
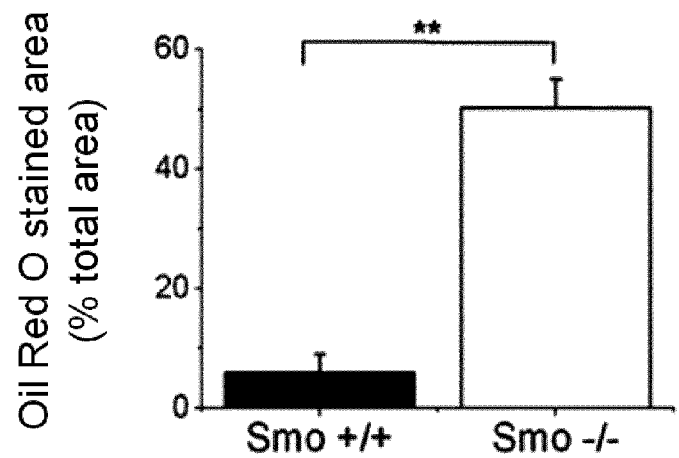

In order to make sure that hepatocyte-specific ablation of Smo is the sole cause for the observed phenotypic features, a second transgenic model (herein referred to as "SAC-mice") was generated that uses a different mechanism for hepatocyte specific ablation of Smo. SAC-mice were generated by crossing $Smo^{flox/flox}$-mice ($Smo^{tm2Amc}$/J mice) with transgenic mice expressing the Cre-recombinase open reading frame (ORF) under the control of both, mouse albumin regulatory elements and a-fetoprotein enhancers (so-called AlfpCre transgenic mice). The F1 generation was back-crossed to generate homozygous $Smo^{flox/flox}$ alleles. Cre-recombinase expression starts already in the fetal state thereby leading to ablation of Smo in the fetal state. All features described for SLC-KO mice were found similar in male and female SAC-KO mice, although they were induced earlier (FIG. 2a,b). In particular hepatic steatosis and lipodystrophy were pronounced. It was observed that some SAC-mice develop first signs of non-alcoholic steatohepatitis (NASH) at an age of 4-5 months.

To demonstrate, that inhibition of Smo by an inhibitory molecule causes the same symptoms, hepatocytes were cultured in vitro in the presence of the Smo inhibitor cyclopamine.

Cyclopamine Experiments.

Cyclopamine (Sigma) was dissolved in DMSO (10 mM). Mouse and human hepatocytes were incubated for 72 h in the presence of 10 µM Cyclopamine. Control cultures were incubated with culture medium containing vehicle (0.1% DMSO).

Additional Lipid Staining.

Fluorescent staining of neutral lipids in hepatocytes was performed using Nile red (Biomol). Hepatocytes were fixed with 4% buffered paraformaldehyde for 10 min. For Nile red staining, a 200 nM working solution in phosphate-buffered saline (PBS) was prepared from a 1 mM stock solution in DMSO and was added directly to the fixed cells. After 20 min of incubation at room temperature cells were washed in PBS. Nuclei were counterstained with DAPI (Sigma).

Figure 20:
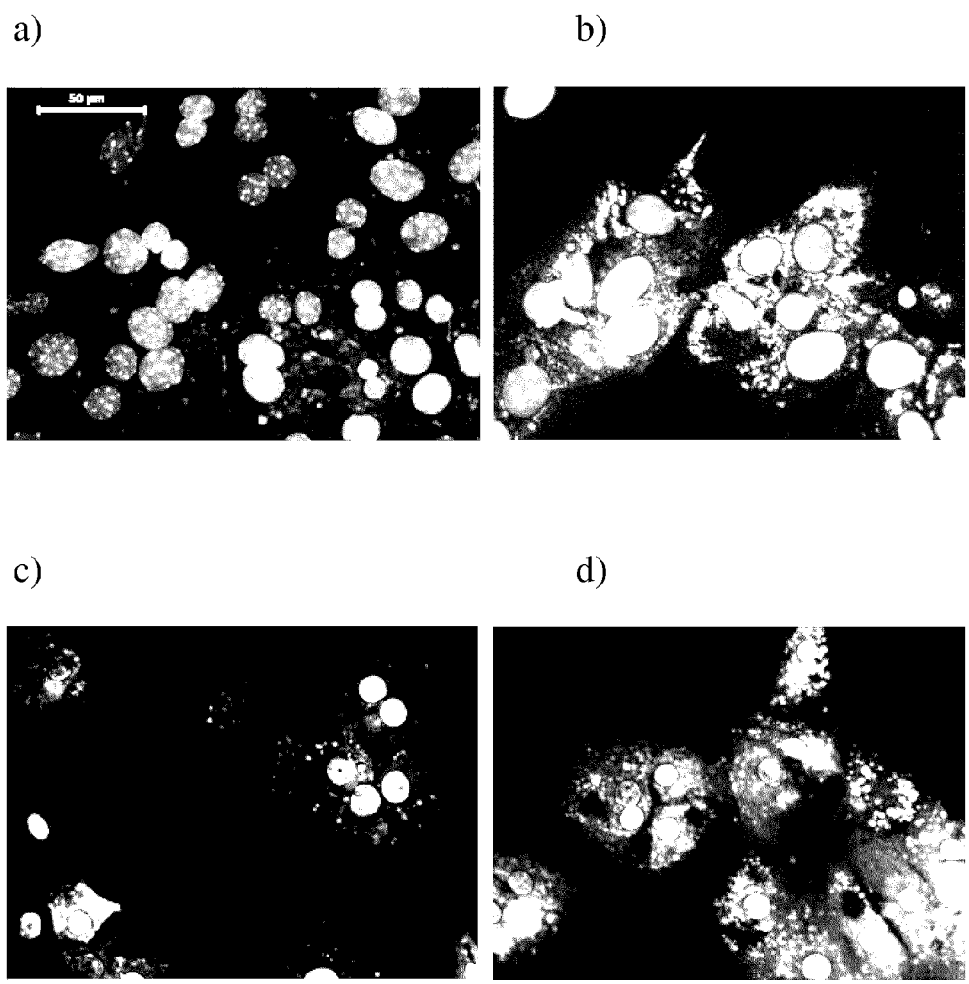
FIG. 20 Influence of cyclopamine on accumulation of neutral lipids in cultured mouse and human hepatocytes. Mouse (a and b) and human (c and d) hepatocytes were cultured in the absence (a, c; vehicle only) or presence (b, d) of 10 μM cyclopamine (in 0.1% DMSO). After 72 h cultures were fixed and stained with Nile red. Bar represents 50 μm.

It could be shown, that in murine and human hepatocytes inhibition of Smo by cyclopamine resulted in marked steatosis (FIGS. 20b and d).

EXAMPLE 2

Figure 3:
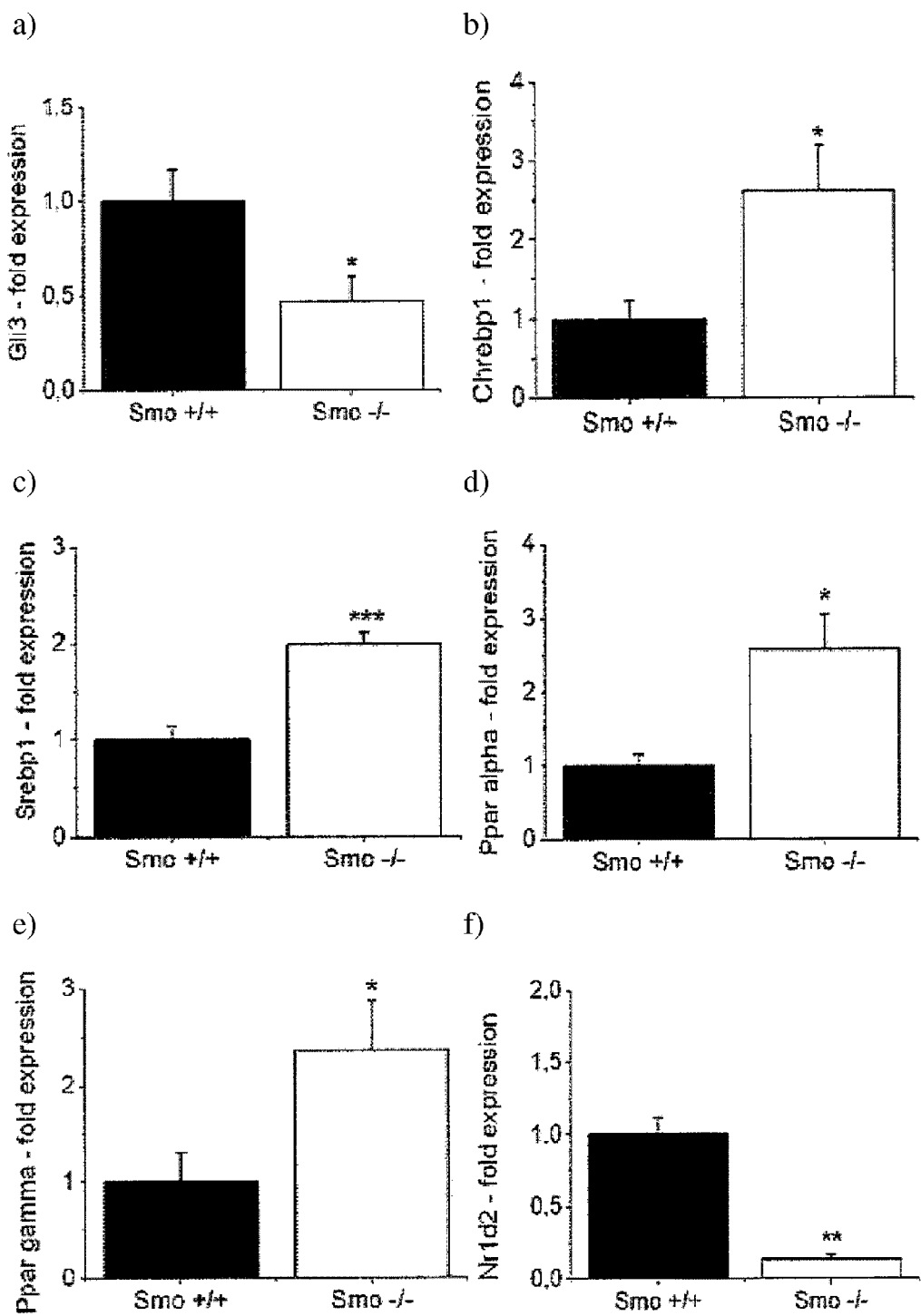
FIG. 3 Hepatocyte specific knockout of Smo is associated with a) downregulation of transcription factor GLI3; upregulation of lipogenic transcription factors: b) Chrebp1, c) Srebp1, d) peroxisome proliferator-activated receptor-α (PPAR-α), e) PPAR-γ; and downregulation off) Nr1d2.

Hepatocyte-Specific Knock-Out of Smo is Associated with Downregulation of GLI3 and Induction of Lipogenesis The influence of the hepatocyte-specific Smo knock-out on the relative expression of several transcription factors was determined by quantitative RT-PCR in isolated hepatocytes from WT and KO SLC-mice (FIG. 3).

Isolation and Cultivation of Primary Hepatocytes.

Primary hepatocytes from SLC mice were isolated by collagenase perfusion of the liver. Cell suspension was carefully cleared from non-parenchymal cells by differential centrifugation. Finally, hepatocytes were suspended in Williams Medium E containing 10% fetal calf serum and further additions as described (Klingmüller et al., 2006), and were plated onto 6-well or 12-well plates precoated with collagen type I (Klingmüller et al., 2006; Gebhardt et al., 1982). After 4 h, serum-free medium was used throughout cultivation. Cryopreserved human hepatocytes were purchased from TebuBio (Offenbach, Germany). They were thawed according to existent protocols (Klingmüller et al., 2006) and cultured in 6-well plates at the same cell density as mouse hepatocytes. Culture conditions were the same as described above for mouse hepatocytes except for the omission of dexamethasone after 4 h.

RNA Preparation and Quantitative Real-Time PCR (qRT PCR).

Total RNA from hepatocytes, liver tissue and other organs was extracted using TRIzol (Peqlab, Erlangen). Total RNA from adipose tissue was extracted using the RNeasy Lipid Tissue mini Kit (Quiagen, Hilden). RNA was reverse transcribed using oligo(dt) primers and IM Promm II reverse transcriptase (Promega). The resulting cDNA samples were then quantified for each test gene using target gene-specific primers designed using the online tools Universal ProbeLibrary Probe-Finder software, Perl Primer and Primer 3.

The following primers were used for real time PCR:

TABLE 2

|  |  |  | SEQ ID No. |
|---|---|---|---|
| GLI3 | fw | ctggcttgattgttcacgag | 23 |
|  | rev | cagccctcatgctcacagac | 24 |
| Chrebp1 | fw | acatcagcgctttgaccag | 9 |
|  | rev | taaaggtcggatgaggat | 10 |
| Srebp1 | fw | aagcgctaccggtcttctatc | 37 |
|  | rev | tgtgcacttcgtagggtcag | 38 |
| Ppar-α | fw | cgtacggcaatggctttatc | 31 |
|  | rev | tcatctggatggttgctctg | 32 |
| Ppar-γ | fw | atggaagaccactcgcattc | 33 |
|  | rev | gctttatccccacagactcg | 34 |
| Nr1d2 | fw | acagaaatagttacctgtgcaacact | 29 |
|  | rev | gacttgctcataggacacacca | 30 |

The levels of all mRNA transcripts were determined in duplicate by qRT-PCR using the Light Cycler® 2.0 Instrument and the LightCycler® FastStart DNA Master PLUS SYBR Green I (Roche). Using the standard curve method, the absolute quantitation of specific PCR products for each primer set was generated. For normalization, β-actin was amplified from each sample.

It could be demonstrated that GLI3 is significantly downregulated upon inhibition of hedgehog signaling via Smo. Further it could be shown that the expression of activators of lipogenesis, namely Chrebp1, Srebp1, PPAR-α and PPAR-γ, was significantly upregulated. To the contrary, the expression of Nr1d2, a regulatory molecule involved in lipid homeostasis, is downregulated.

EXAMPLE 3

Silencing of GLI Family Members in Hepatocytes Using siRNA

To analyze the role of GLI family members in C57Bl/6-N hepatocytes on gene expression, murine hepatocytes were isolated and cultured for 72 h upon transfection with siRNA silencing either GLI1, GLI2 or GLI3.

RNA Interference.

GLI1-, GLI2- and GLI3-specific siRNAs and respective scrambled control siRNAs were purchased from Invitrogen. The following double stranded siRNAs were used for inhibition of GLI1, GLI2 and GLI3:

TABLE 3

|      |                              | SEQ ID No. |
|------|------------------------------|------------|
| GLI1 | UGGAGAACCUUAGGCUGGAUCAGCU    | 1          |
|      | AGCUGAUCCAGCCUAAGGUUCUCCA    | 2          |
| GLI2 | CCACAACCACAACGUUGCUCAGACA    | 3          |
|      | UGUCUGAGCAAGCUUGUGGUUGUGG    | 4          |
| GLI3 | UAGCAAGGCCAUCUUGGUCUUCAGG    | 5          |
|      | CCUGAAGACCAAGAUGGCCUUGCUA    | 6          |

Freshly isolated hepatocytes were seeded at a density of 100.000 cells per well of 12-well plates in normal culture medium containing 10% FCS. After 4 h, serum-free medium was used and chemically synthesized siRNAs (10 nmol for GLI2 and GLI3, 50 nM for GLI1) were transfected with Interferin from Peqlab (Erlangen) according to the manufacturer's instructions. Twenty-four hours after transfection, the medium was changed and fresh medium without siRNA was added. Changes in gene expression were analyzed by qRT PCR at different time points up to 72 h post-transfection as indicated in figure legends using primers as described above in Example 2 and the following additional primers:

TABLE 4

|        |                              | SEQ ID No. |
|--------|------------------------------|------------|
| Elovl6 | fw tctgggcttatgcatttgtg      | 13         |
|        | rev acaggagcacagtgatgtgg     | 14         |
| Fasn   | fw tagagggagccagagagacg      | 15         |
|        | rev ttggcccagaactcctgtag     | 16         |

Figure 4:
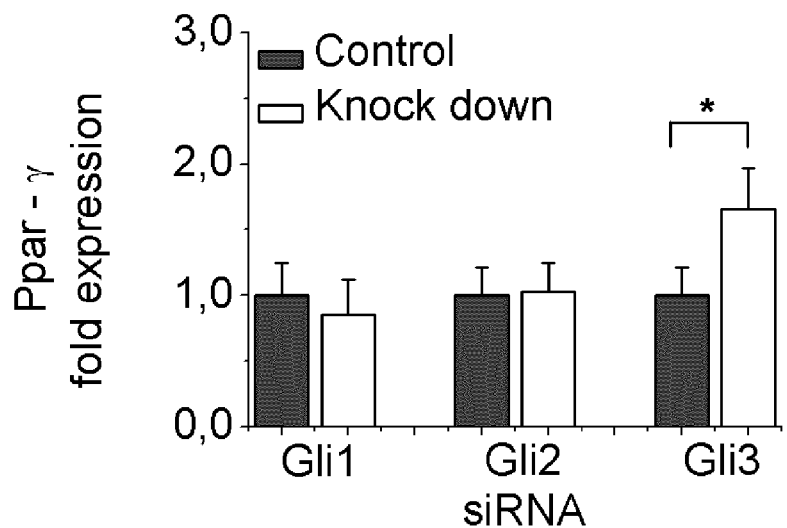
FIG. 4-7: Silencing of GLI family members in murine hepatoctes using siRNA. C57Bl/6-N hepatocytes were transfected with siRNA against GLI1, GLI2 and GLI3 (open bars) or nonsense RNA (control, black bars). mRNA levels of the indicated genes were quantified by RT-PCR. Only loss of GLI3 is associated with increased levels of lipogenic transcription factors peroxisome proliferator-activated receptor-γ (PPAR-γ, FIG. 4) and sterol regulatory element-binding protein 1 (SREBP1, FIG. 5) and lipogenic enzymes ELOVL fatty acid elongase 6 (Elovl6, FIG. 6) and fatty acid synthase (Fasn, FIG. 7).
Figure 5:
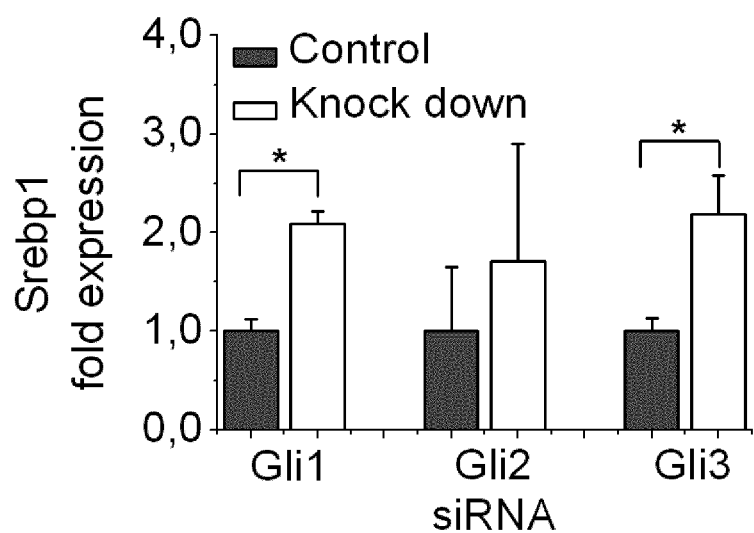
Figure 6:
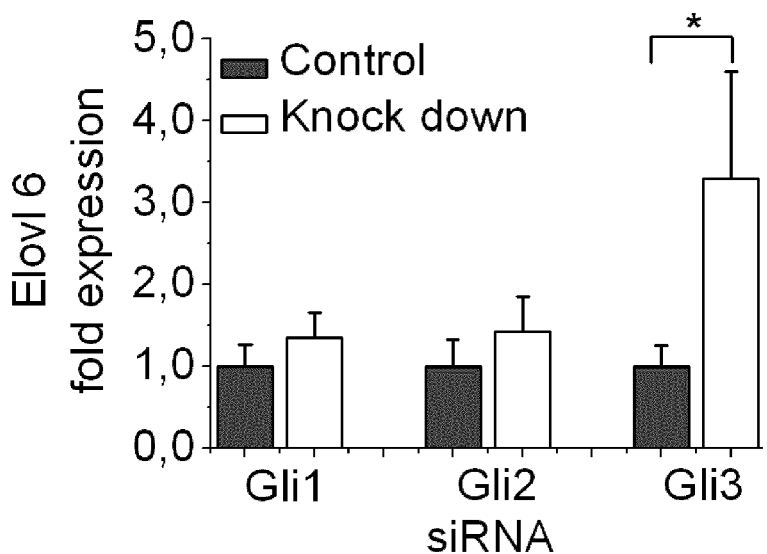
Figure 7:
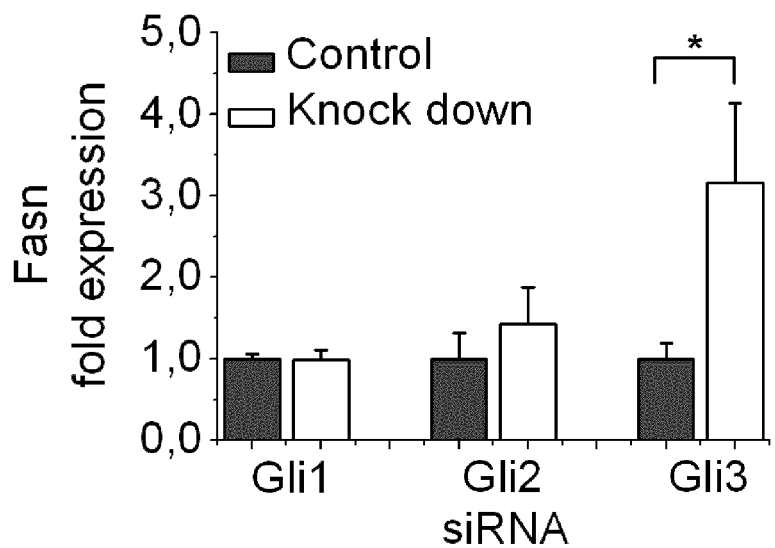

It was demonstrated that silencing of GLI3 and not GLI1 or GLI2 is associated with significantly increased expression of lipogenic transcription factors PPAR-γ (FIG. 4), and Srebp1 (FIG. 5). Accordingly, an increased expression of lipogenic enzymes ELOVL fatty acid elongase 6 (Elovl6, FIG. 6) and fatty acid synthase (Fasn, FIG. 7) was observed.

Figure 8:
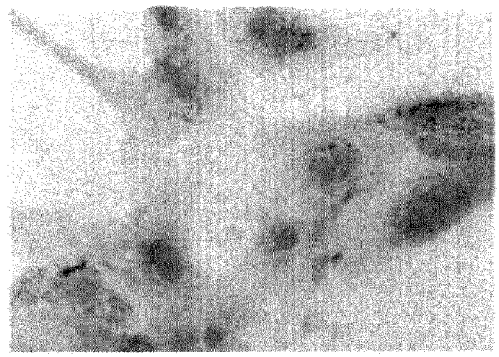
FIG. 8 Staining of neutral lipids by Oil red O in cultured hepatocytes transfected with a) mock, b) GLI1 siRNA, c) GLI2 siRNA and d) GLI3 siRNA determined after 72 h.
Figure 8:
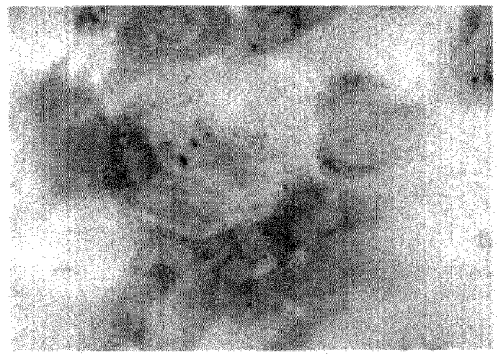
Figure 8:
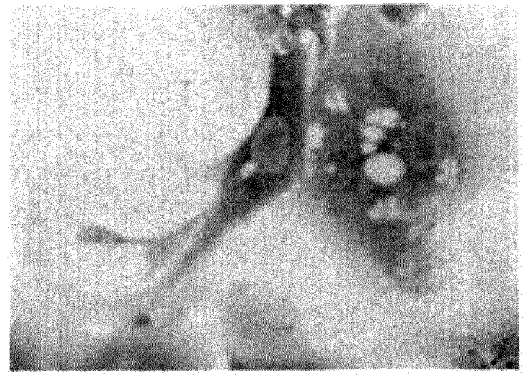
Figure 8:
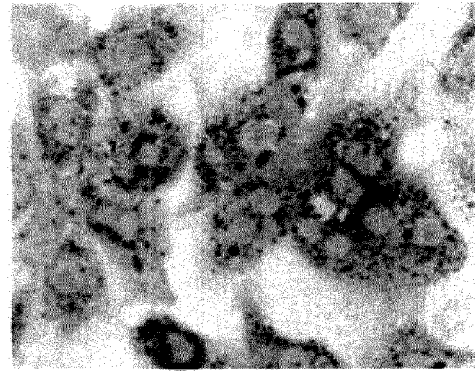

Oil red O staining of neutral lipid oils of C57Bl/6-N hepatocytes cultured upon siRNA transfection showed that silencing of GLI3 (FIG. 8d) lead to pronounced accumulation of fat droplets. On the contrary neither GLI1 siRNA (FIG. 8b) nor GLI2 siRNA (FIG. 8c) was capable of mediating this effect. Hepatocytes transfected with GLI1 or GLI2 siRNA showed a comparable phenotype as wild type hepatocytes (FIG. 8a).

The experiments demonstrate that downregulation of GLI3 but not downregulation of GLI1 or GLI2 is capable of promoting gene expression patterns associated with the development of hepatic steatosis.

Taken together, the data indicate that hedgehog signaling in hepatocytes appears to be an important regulatory mechanism preventing early stages of hepatic steatosis. Disruption of hedgehog signaling in hepatocytes leads to downregulation of GLI3, which—either by being directly silenced, e.g. by siRNA or downregulated by inhibited hedgehog signaling in Smo knock-out mice—was shown to be associated with gene expression patterns and phenotypes of hepatic steatosis.

EXAMPLE 4

Silencing of Supressor of Fused (Sufu) in Hepatocytes Using siRNA Leads to Activation of GLI3

To demonstrate that not only downregulation of GLI3 is associated with symptoms of hepatic steatosis but also activation of GLI3 is capable of ameliorating disease symptoms, murine C57BL/6-N hepatocytes were transfected with siRNA silencing Sufu according to the following nucleic acid sequences:

```
                                           SEQ ID No. 7
    CCCUUGGACUAUGUUAGCAUGUACA,

SEQ ID No. 8
    UGUACAUGCUAACAUAGUCCAAGGG.
```

Sufu is a known inhibitor of hedgehog signalling. The transfection of hepatocytes with siRNA and real time PCR was performed as described in Example 3. The following additional primers were used:

TABLE 5

|       |                              | SEQ ID No. |
|-------|------------------------------|------------|
| Sufu  | fw cttccagtcagagaacacct      | 43         |
|       | rev ttgggctgaatgtaactc       | 44         |
| Ihh   | fw gctcaccccaactacaatc       | 27         |
|       | rev gcggccctcatagtgtaaag     | 28         |
| GLI2  | fw actttctccacaccctgctg      | 21         |
|       | rev ggctgcgaggctaaagagtc     | 22         |
| GATA4 | fw ggaagacaccccaatctcg       | 17         |
|       | rev catggcccacaattgac        | 18         |

Figure 9:
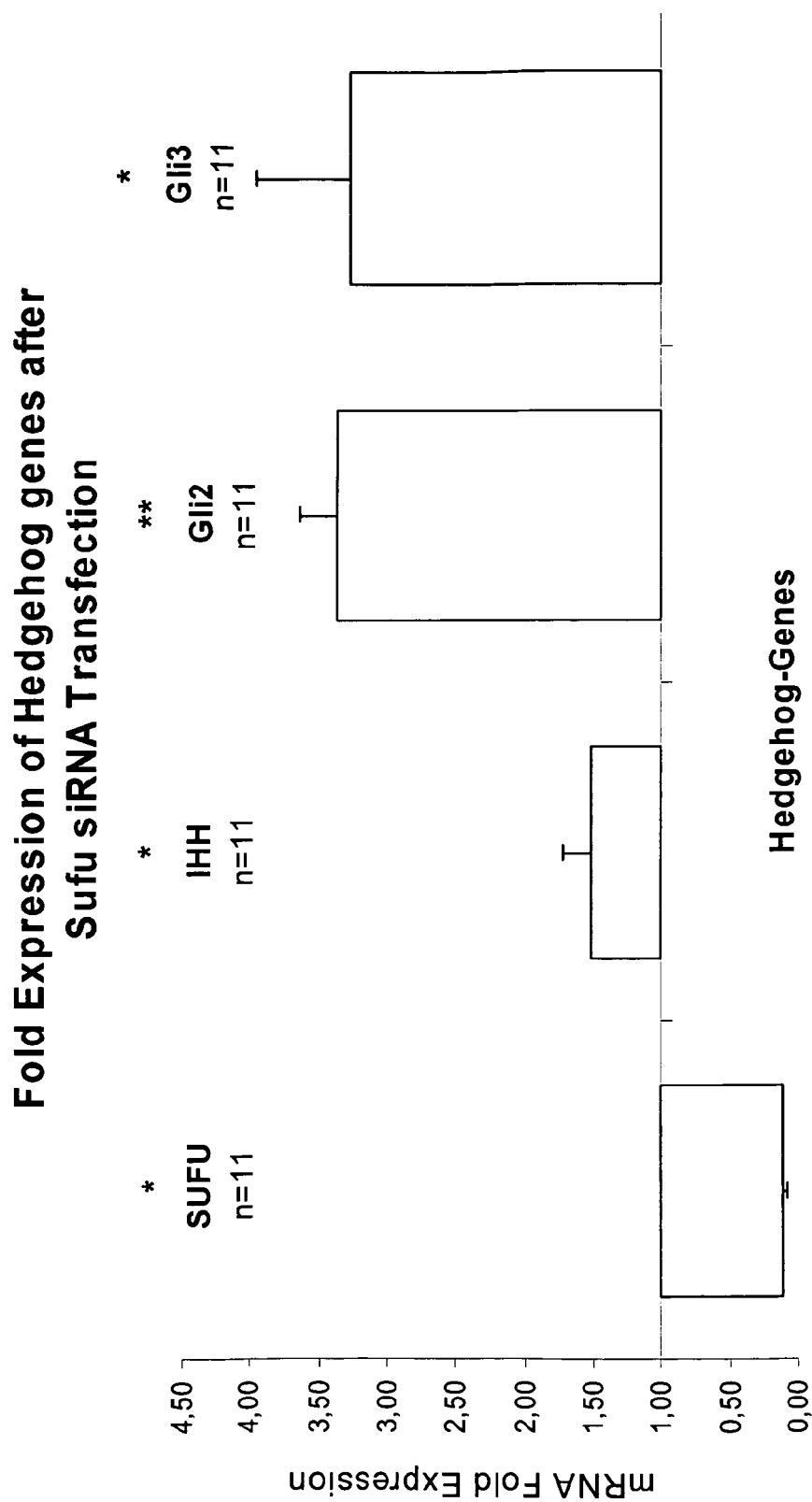
FIG. 9 Silencing of Sufu in hepatocytes by siRNA transfection leads to decreased expression of genes associated with hedgehog-signaling.

Successful silencing of Sufu was associated with increased expression of hedgehog related genes, such as Indian hedgehog (IHH), GLI2 and GLI3 (FIG. 9). Thereby it was demonstrated that silencing of Sufu in hepatocytes is indeed capable of activating GLI3.

Figure 10:
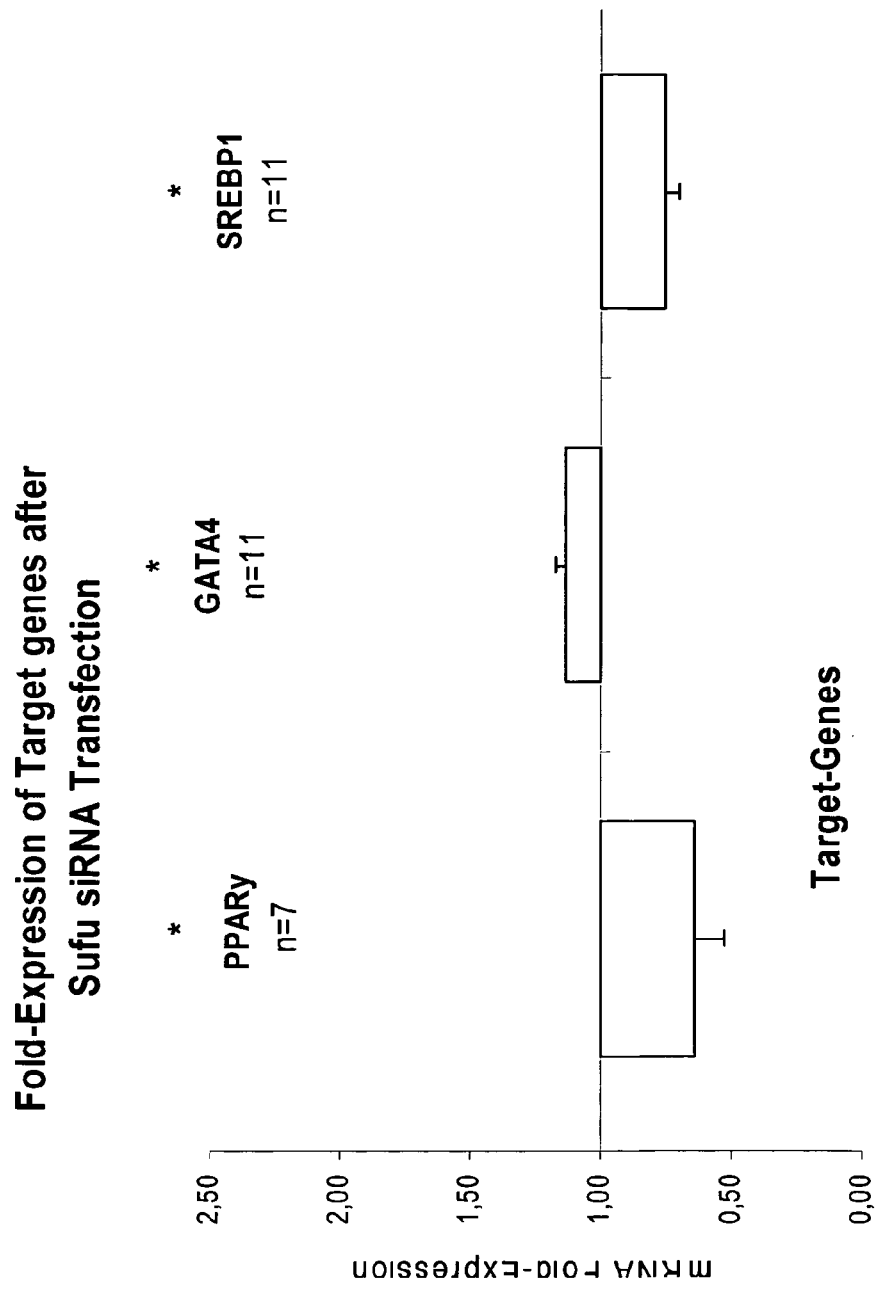
FIG. 10 Silencing of Sufu in hepatocytes by siRNA transfection leads to decreased expression of lipogenic transcription factors PPAR-γ and Srebp1 and increased expression of GATA4.

Further, it was shown that hepatocellular expression of lipogenic transcription factors PPAR-γ and Srebp1 was reduced (FIG. 10). Thereby it is demonstrated that activation of GLI3 by inhibiting Sufu is sufficient to downregulate expression of lipogenic transcription factors and enzyme associated with hepatic steatosis.

EXAMPLE 5

Increased Fat Deposits Upon Hepatocyte-Specific Knock-Out of Smo

Apart from signs of hepatic steatosis SAC-mice as described in example 1 showed massively increased fat deposition. As shown in the experiments described in examples 1-3 disruption of hedgehog signaling is associated with enhanced expression of lipogenic enzymes.

Figure 12:
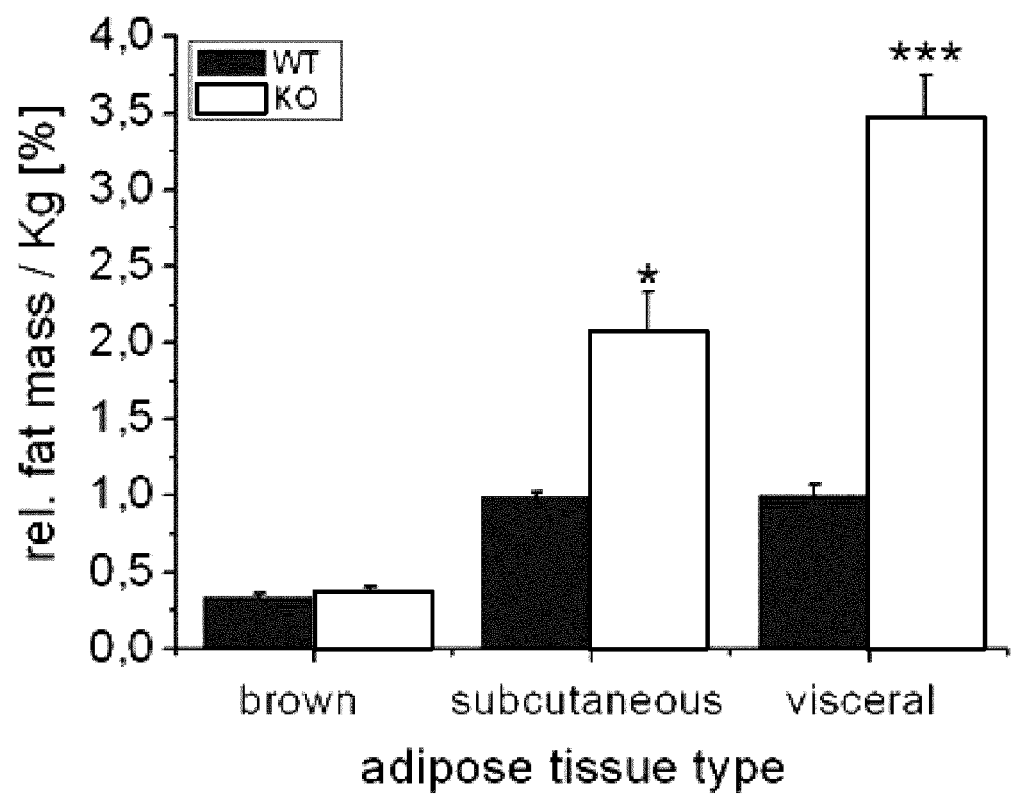
FIG. 12 Increased visceral fat deposition in Smo$^{-/-}$ mice.
Figure 13:
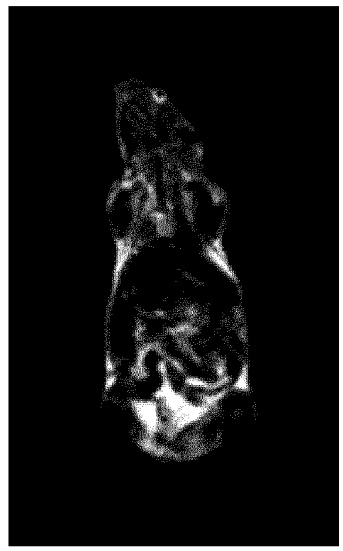
FIG. 13 MRT Images of wild type (Smo$^{+/+}$) and knock-out mice (Smo$^{-/-}$). Pictured are a), b) female, and c), d) male mice. White areas indicate body fat.
Figure 13:
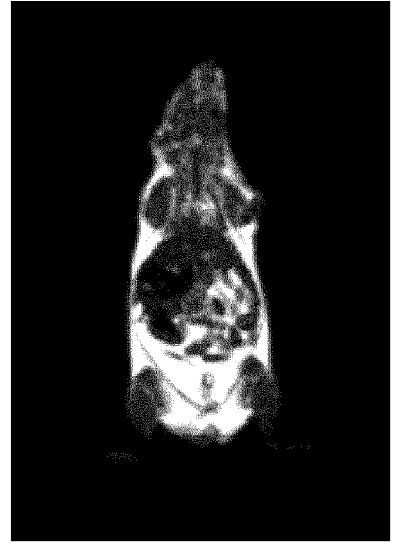
Figure 13:
Figure 13:

A detailed analysis of the fat deposits of Smo knock-out mice revealed significant increases of subcutaneous and especially visceral fat deposits. Whereas the relative fat mass of subcutaneous fat doubles upon Smo knock-out, the relative mass of visceral fat is about 3.5 times as much as observed for wild type mice (FIG. 12, FIG. 13).

Figure 19:
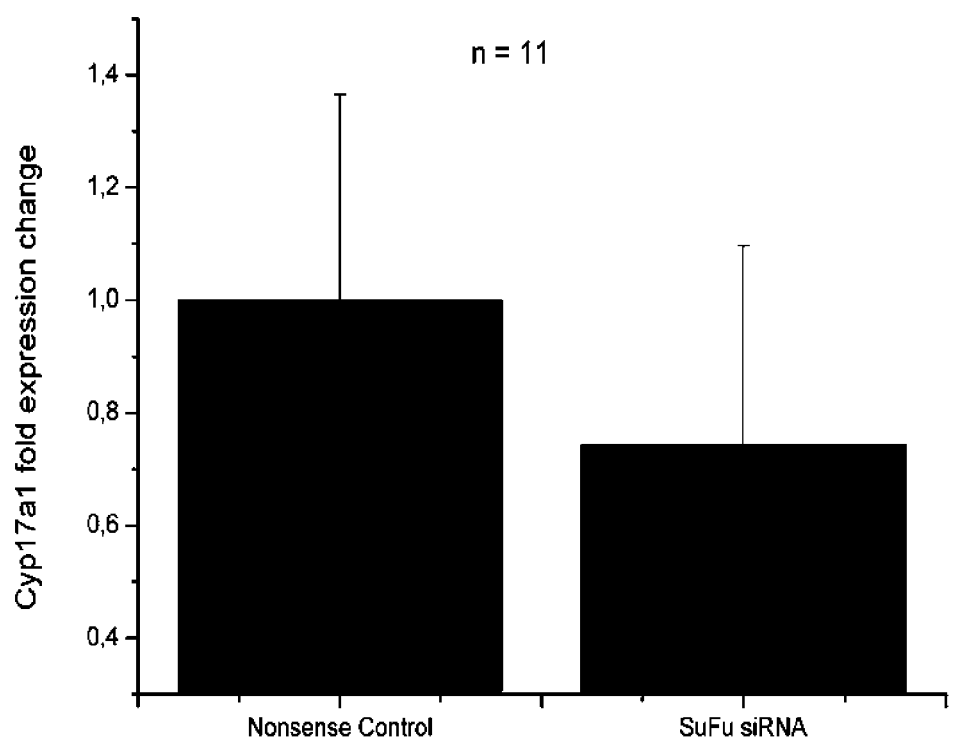
FIG. 19 Silencing of Sufu in hepatocytes by siRNA transfection leads to decreased expression of Cva17a1.

The phenotype observed in SAC-mice indicates a crucial role of hedgehog signaling in hepatocytes for regulation of accumulation and localization of body fat. It is likely that the fat accumulation is supported by increased serum levels of dihydroepiandrosterone (DHEA, FIG. 17). By activating GLI3 through downregulation of Sufu, hepatocellular overexpression of steroid 17-alpha-monooxygenase (Cyp17A1) could be reversed (FIG. 19).

EXAMPLE 6

Figure 14:
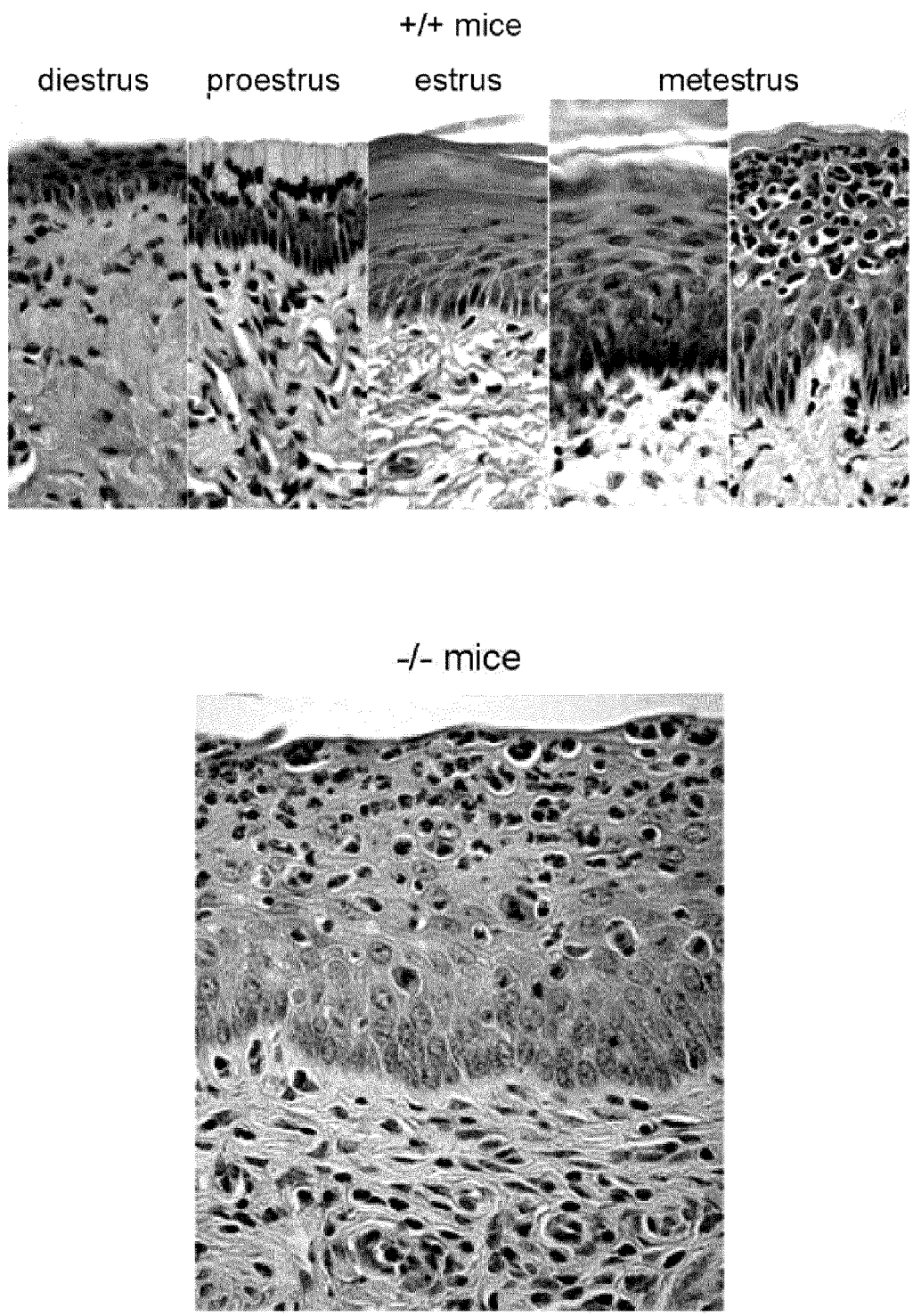
FIG. 14 Infertility of female Smo knock-out mice is associated with symptoms similar to PCOS. Wild type mice (Smo$^{+/+}$) show a normal cycle of the vaginal epithelium, while knock-out mice (Smo$^{-/-}$) constantly show a somewhat disturbed epithelium best resembling the metestrus phase. (Hematoxilin & eosin staining)

Symptoms Similar to PCOS in Homozygous Female SAC-Mice are Associated with Infertility of Said Mice It was surprisingly found, that female SAC-mice with a homozygous Smo knock-out failed to reproduce and appeared to be infertile. Whereas heterozygous and Smo+/+ mice undergo a regular sexual cycle, homozygous SAC-mice do not and remain in the metestrus phase (FIG. 14).

Figure 15:
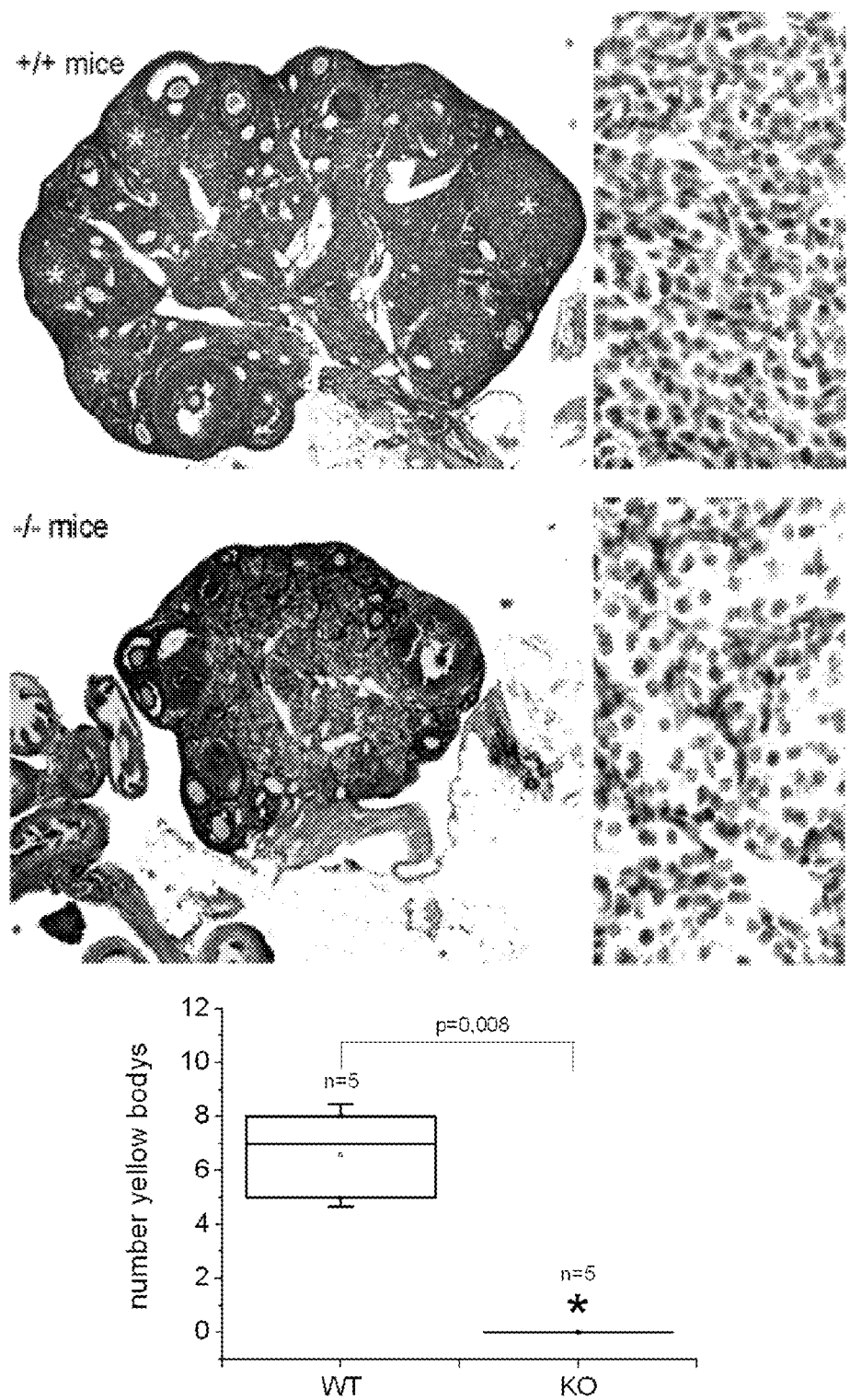
FIG. 15 Histology of ovary of wild type mice (+/+ mice) presenting normal yellow bodies (corpi luteum; stars) and Smo knock-out mice (−/− mice) lacking yellow bodies, but demonstrating many follicular cysts. Left pictures indicate a histological section of the ovary (stars indicate the corpus luteum), the right pictures depict intersticial gland cells. Bottom graph: comparison of the number of yellow bodies (corpi luteum) per ovary in wild type and Smo knockout mice.

A histological analysis of the ovary revealed that homozygous SAC-mice completely fail to form yellow bodies (corpi luteum) (FIG. 15). Instead, they frequently contain follicular cysts. These symptoms equal the symptoms described for polycystic ovary syndrome (PCOS).

Liver cells were analyzed by quantitative Real time PCR using a protocol according to Example 3 with the following primers:

TABLE 6

| | | SEQ ID No. |
|---|---|---|
| Cyp17A1 | fw catcccacacaaggctaaca | 11 |
| | rev cagtgcccagagattgatga | 12 |
| STAR | fw ttgggcatactcaacaacca | 41 |
| | rev acttcgtccccgttctcc | 42 |
| Hsd3β | fw tggacaaagtattccgaccag | 25 |
| | rev aggcctccaataggttctg | 26 |
| Shgb | fw tctcccttggggctttac | 39 |
| | rev tcccaacttcacctctcctg | 40 |

Figure 16:
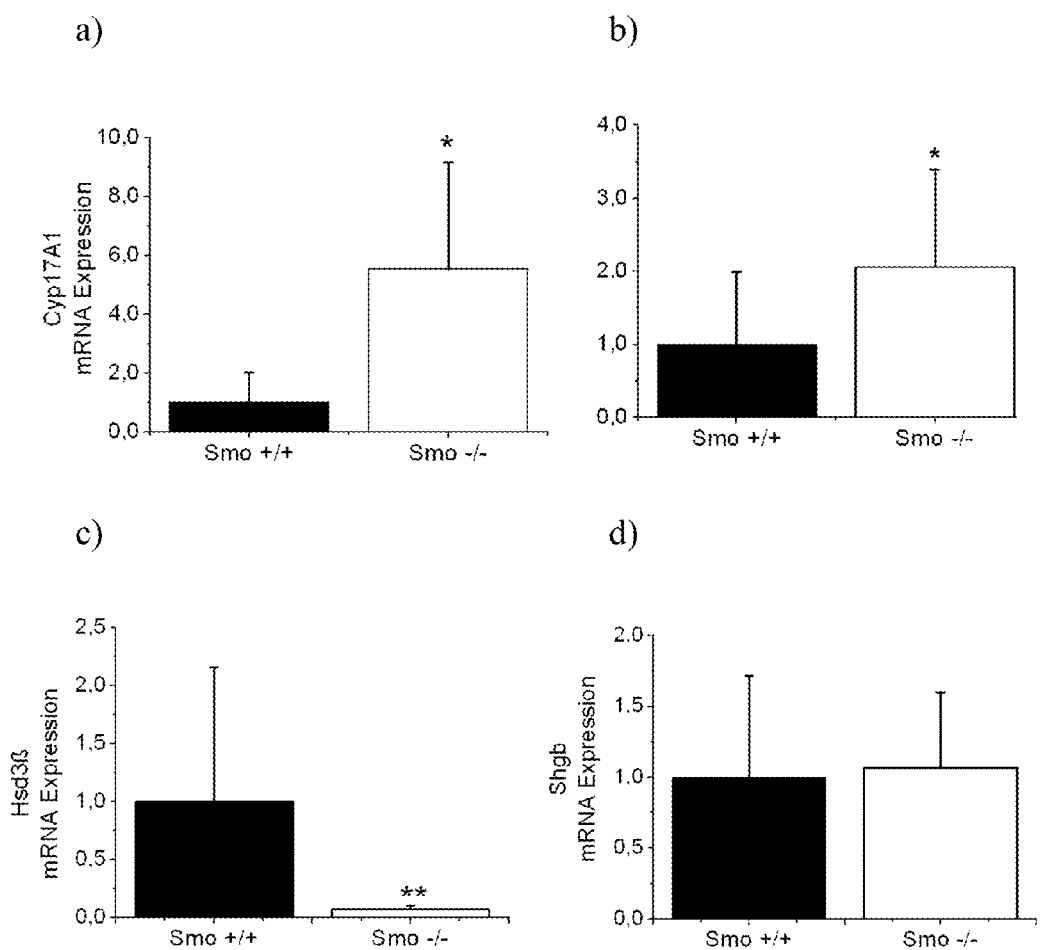
FIG. 16 Hepatocyte-specific knockout of Smo is associated with hepatocellular a) upregulation of steroid 17-alpha-monooxygenase (Cyp17A1); b) upregulation of steroidogenic acute regulatory protein (STAR); c) downregulation of 3-β-hydroxysteroid dehydrogenase/Δ-5-4 isomerase (Hsd3β) and d) comparable levels of sex hormone-binding globulin (Shgb).
Figure 18:
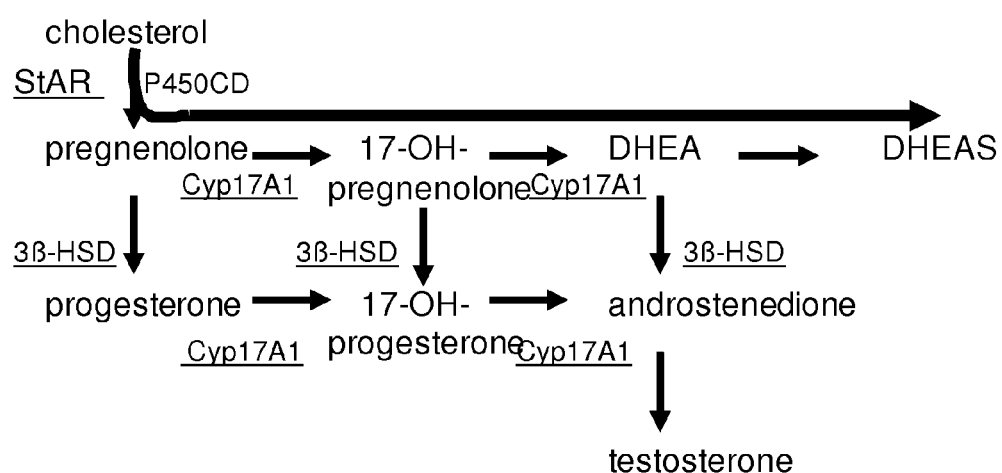
FIG. 18 Schematic reaction table for biosynthesis of steroid hormones (androgens) in Smo−/− mice. In Smo−/− mice steroidogenic acute regulatory protein (STAR) and steroid 17-alpha-monooxygenase (C17A1) are upregulated and 3-β-hydroxysteroid dehydrogenase/Δ-5-4 isomerase (Hsd3β) is downregulated (see FIG. 16). The bold arrow illustrates the predominated synthetic route leading to dihydroepiandrosterone-sulfate (DHEAS) in homozygous Smo knock-out mice (−/− mice).

It was demonstrated that livers of homozygous SAC-mice overexpress steroid 17-alpha-monooxygenase (Cyp17A1) and steroidogenic acute regulatory protein (StAR) and show decreased expression of 3-β-hydroxysteroid dehydrogenase/Δ-5-4 isomerase (Hsd3β, FIG. 16), all of which are enzyme involved in synthesis of steroid hormones as depicted in the scheme in FIG. 18.

Figure 17:
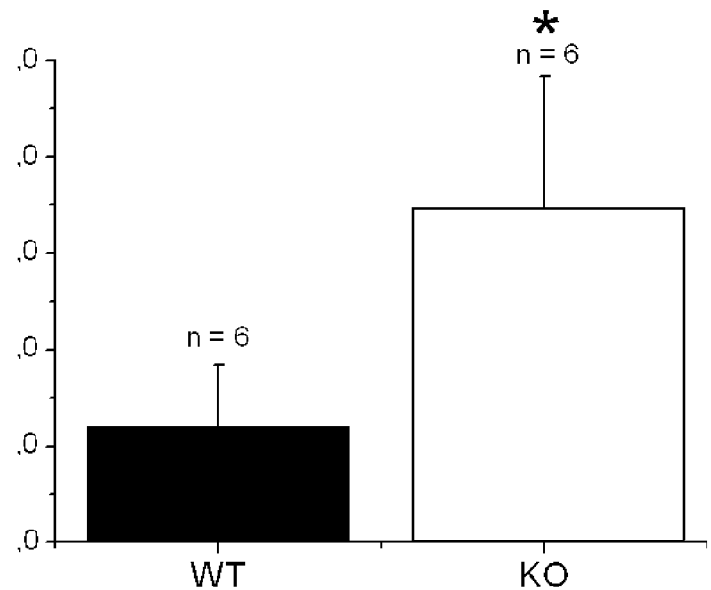
FIG. 17 Hepatocyte-specific knockout of Smo in 12 week old female mice (−/− mice) is associated with significantly increseased serum levels of dihydroepiandrosterone-sulfate (DHEAS).

By inhibition of Hsd3β, precursors of androstenedione (like progesterone, pregnenolone) cannot be converted to androstenedione which leads to increased levels of dihydroepiandrosterone (DHEA) that is further converted in the liver to its sulphated version DHEA-S (scheme in FIG. 18). Homozygous SAC-mice show significantly elevated levels of DHEA-S in serum (FIG. 17).

EXAMPLE 7

IGF1 and IGFBP1 are Surrogate Markers in Mouse Serum of Hepatic Hedgehog Activity and Reflect the Activity Status of the Transcription Factor Gli3

Since the activity status of hedgehog signalling in liver cannot be detected by non-invasive techniques, we were interested in finding suitable surrogate markers that can be measured in the serum.

Figure 21:
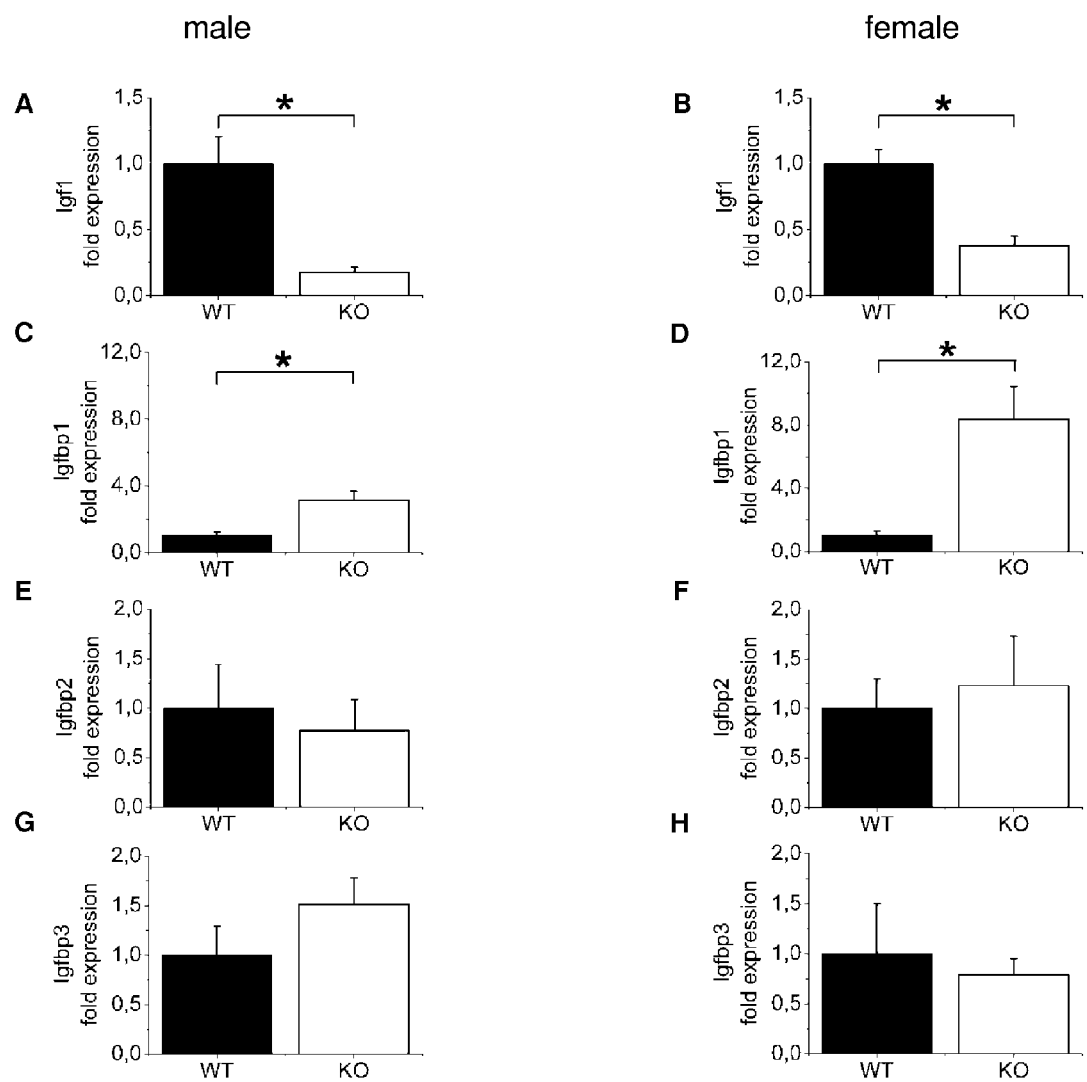
FIG. 21 Hepatic expression levels of IGF signalling components. A,B: Igf1, C,D: Igfbp1, E,F: Igfbp2 and G,H: Igfbp3 in isolated hepatocytes of 12 weeks old male SAC-WT (n=7) and SAC-KO (n=7) (A,C,E,G) and female SAC-WT (n=7) and SAC-KO (n=5) (B,D,F,H). Data represent relative means±SEM; *, $p<0.05$.
Figure 22:
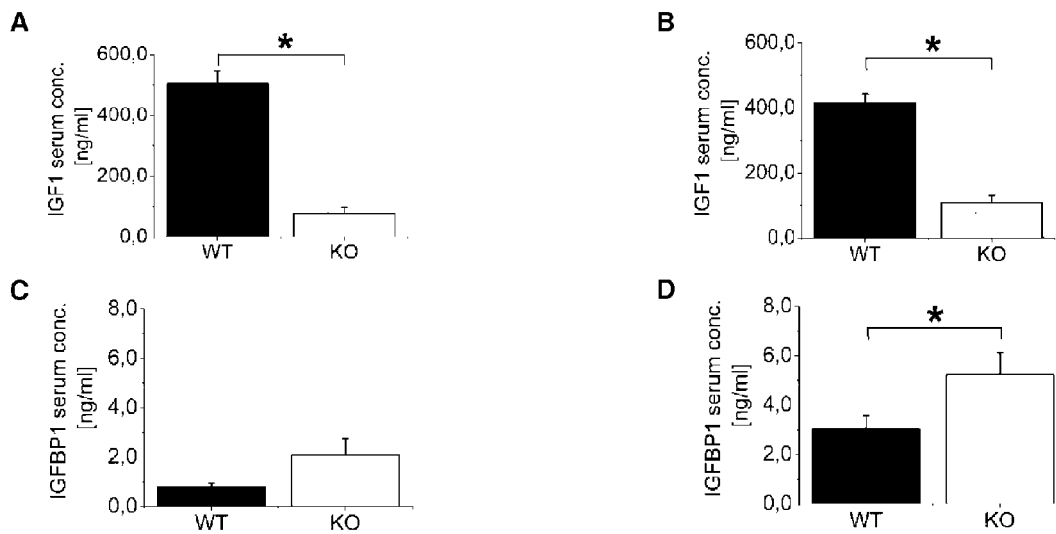
FIG. 22 Serum levels of circulating IGF1 (A,B) and IGFBP1 (C,D) A,C: male SAC-WT(n=9) and SAC-KO (n=8) mice and B,D: female SAC-WT (n=11) and SAC-KO (n=13) mice. Data presented as means±SEM; *, $p<0.05$.

By measuring the mRNA levels of IGF1 and IGFBP1 in the livers of SAC-mice (described in examples 1, 5, and 6) at the age of 12 month, a significant downregulation of IGF1 mRNA was found in males (FIG. 21A) and females (FIG. 21B). In contrast, mRNA for IGFBP1 was upregulated significantly in males (FIG. 21C) and females (FIG. 21D). The mRNA levels of IGFBP2 an IGFBP3 were not changed in mouse livers of both genders (FIG. 21E-H). Accordingly, the serum levels of IGF1 protein and IGFBP1 protein were down- and upregulated, respectively, in male (FIG. 22A, C) and female (FIG. 22B, D) mice. These results fit with the known effects of IGF1 and IGFBP1 on body size and can at least partially explain why mice with hepatocyte-specific knockout of Smo have a smaller size and lower body weight (see example 1). Furthermore, they clearly show that the serum levels of both proteins can be used as surrogate markers for the activity of hepatic hedgehog signalling.

Figure 23:
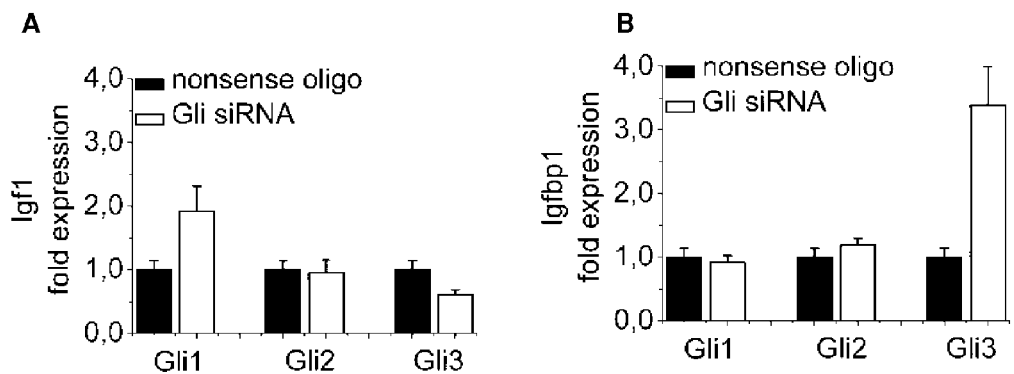
FIG. 23 Effect of silencing of Gli family members in murine hepatocytes using siRNA on expression levels of (A) IGF1, and (B) IGFBP1. Transfection was performed as in FIG. 4. Data represent relative means±SEM; *, $p<0.05$.

Detailed analysis of the influence of silencing of Gli family members in hepatocytes using siRNA (see example 3) revealed that Gli3 siRNA downregulates IGF1 mRNA (FIG. 23A) and upregulated IGFBP1 mRNA (FIG. 23B). These results are compatible with the known fact that Gli3 may have both, activator and repressor activities at the transcriptional level. Thus, Gli3 seems to act as a direct transcriptional activator of IGF1, while is seems to act as an indirect transcriptional repressor of IGFBP1 in hepatocytes.

Figure 24:
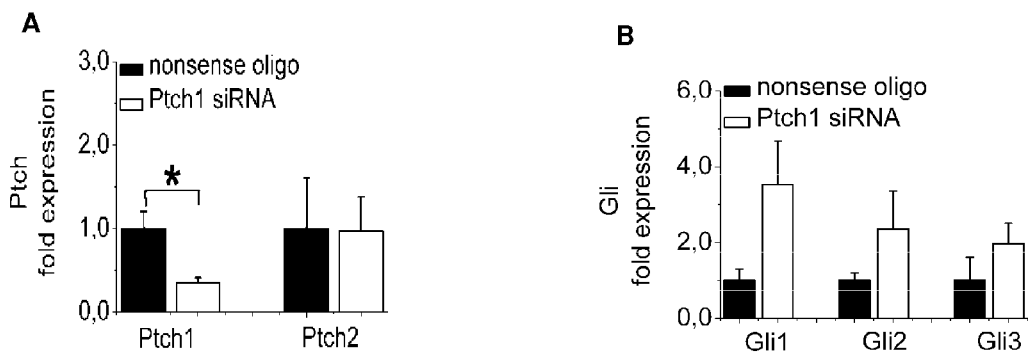
FIG. 24 Effect of silencing of Patched (nail) in marine hepatocytes using siRNA on expression levels of (A) Ptch 1 and Ptch2, and (B) the three Gli factors. Data represent relative means±SEM; *, $p<0.05$.

An independent confirmation of these findings is provided by the activation of hedgehog signalling in cultured hepatocytes due to silencing of the hedgehog receptor Ptch1 by siRNA. Silencing of Ptch1 but not Ptch2 by Ptch1 siRNA within 48 h is shown in FIG. 24 A indicating specificity of this knockdown. Ptch1 siRNA lead to the upregulation of the expression of all three Gli factors (FIG. 24 B) as well as to upregulation of IGF1 mRNA, and downregulation of IGFBP1 mRNA.

TABLE 7

| Gene | Sequence | SEQ ID No. |
|---|---|---|
| Igf1 | fw tggatgctcttcagttcgtg | 45 |
| | rev gcaacactcatccacaatgc | 46 |
| Igfbp1 | fw ctgccaaactgcaacaagaa | 47 |
| | rev tccatgggtagacacaccag | 48 |
| Igfbp2 | fw cggggcccctggaacatc | 49 |
| | rev ggtattggggttcacacacc | 50 |
| Igfbp3 | fw aatgtgctgagtcccagagg | 51 |
| | rev ggagcatctactggctctgc | 52 |
| Ptch1 | fw cctcctttacggtggacaaac | 53 |
| | rev atcaactcctcctgccaatg | 54 |

TABLE 7 -continued

| Gene | Sequence | SEQ ID No. |
|---|---|---|
| Ptch2 | fw cttctcccacaagttcatgc | 55 |
|  | rev cgatgtcattgttctggtagtcg | 56 |

CITED NON PATENT LITERATURE

Brunton et al. 2009 Biorg. Med Chem Lett 19: 4308-4311
Gebhardt et al. 1982 Eur. J. Cell Biol. 29: 68-76
Greenbaum L E, J Clin Invest 2008 (118) 10: 3263-3265
Klingmüller et al. 2006 Syst. Biol. 153: 433-47
Nunnari et al. 1989 Exp. Mol. Pathol. 51: 1-8
Omenetti at al. (Am J Physiol Gastrointest Liver Physiol 2008 (294), S. G595-G598
Omenetti A et al., Hepatology 2009 (50) 2: 518-527
Sicklick J K et al. (Lab Invest 2005 (85), S. 1368-1380
Sicklick J K et al. Am J Physiol Gastrointest Liver Physiol 2006 (290), S. 859-870
Syn W K et al., Gastroenterology 2009 (137): 1478-1488
Trappoliere M et al. (Eur Rev Med Pharmacol Sci 2005 (9), S. 299-304)

The invention claimed is:

1. A method for treating or preventing a disease associated with reduced Hedgehog signaling in hepatocytes, including the step of administering to an individual in need thereof a therapeutically effective amount of an activator of the Hedgehog signaling pathway selected from the group consisting of:

Sonic hedgehog (Shh), Indian hedgehog (Ihh), Desert hedgehog (Dhh), Smoothened agonist (SAG); compounds according to the following formula (1)

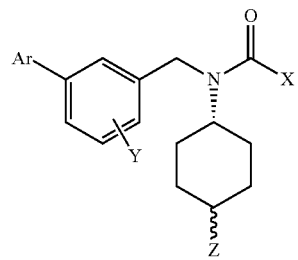

(1)

wherein X is selected from thiophenes or benzothiophenes,
wherein Y is selected from 4- or 6-alkoxy, 4- or 6-alkyl or 4- or 6-halogen,
wherein Z has the structure —(CH$_2$)$_n$—NR$_1$R$_2$,
  wherein R$_1$ and R$_2$ are selected from hydrogen and C1 to C10-alkyl, and
  wherein n is selected from 0, 1 and 2, and
wherein Ar is selected from phenyl or substituted phenyl;
  and combinations thereof.

2. The method of claim 1, wherein the activator of the Hedgehog signaling pathway is administered to at least one hepatocyte of said individual.

3. The method according to claim 1, wherein the disease is associated with imbalanced liver lipid metabolism and/or increased fat deposits.

4. The method of claim 1, wherein the disease is selected from the group consisting of
  polycystic ovary syndrome,
  fatty liver disease,
  non-alcoholic fatty liver disease,
  adiposity, and
  combinations thereof.

5. The method of claim 4, wherein the non-alcoholic fatty liver disease is non-alcoholic Steatosis hepatis or non-alcoholic Steatohepatitis.

6. The method of claim 4, wherein the fatty liver disease is Steatosis hepatis or Steatohepatitis.

7. The method of claim 1, for reducing visceral fat deposition or prevention of visceral fat deposition.

8. The method of claim 1, wherein the activator of the Hedgehog signaling pathway is SAG.

9. A method for activating Hedgehog signaling in hepatocytes comprising administration to an individual in need thereof an activator of the zinc finger protein GLI3 selected from the group consisting of:
  Sonic hedgehog (Shh), Indian hedgehog (Ihh), Desert hedgehog (Dhh), Smoothened agonist (SAG);
  compounds according to the following formula (1)

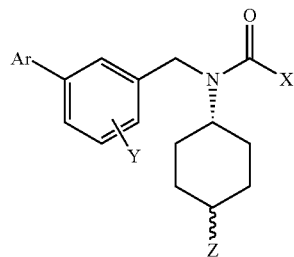

wherein X is selected from thiophenes or benzothiophenes,
wherein Y is selected from 4- or 6-alkoxy, 4- or 6-alkyl or 4- or 6-halogen,
wherein Z has the structure —(CH$_2$)$_n$—NR$_1$R$_2$,
  wherein R$_1$ and R$_2$ are selected from hydrogen and C1 to C10-alkyl, and
  wherein n is selected from 0, 1 and 2, and
wherein Ar is selected from phenyl or substituted phenyl;
  and combinations thereof.

* * * * *

```
                              SEQUENCE LISTING

<160> NUMBER OF SEQ ID NOS: 56

<210> SEQ ID NO 1
<211> LENGTH: 25
<212> TYPE: RNA
<213> ORGANISM: Artificial Sequence
<220> FEATURE:
<223> OTHER INFORMATION: siRNA

<400> SEQUENCE: 1
uggagaaccu uaggcuggau cagcu                                        25

<210> SEQ ID NO 2
<211> LENGTH: 25
<212> TYPE: RNA
<213> ORGANISM: Artificial Sequence
<220> FEATURE:
<223> OTHER INFORMATION: siRNA

<400> SEQUENCE: 2
agcugaucca gccuagguu cucca                                         25

<210> SEQ ID NO 3
<211> LENGTH: 25
<212> TYPE: RNA
<213> ORGANISM: Artificial Sequence
<220> FEATURE:
<223> OTHER INFORMATION: siRNA

<400> SEQUENCE: 3
ccacaaccac aacguugcuc agaca                                        25

<210> SEQ ID NO 4
<211> LENGTH: 25
<212> TYPE: RNA
<213> ORGANISM: Artificial Sequence
<220> FEATURE:
<223> OTHER INFORMATION: siRNA

<400> SEQUENCE: 4
ugucugagca agcuuguggu ugugg                                        25

<210> SEQ ID NO 5
<211> LENGTH: 25
<212> TYPE: RNA
<213> ORGANISM: Artificial Sequence
<220> FEATURE:
<223> OTHER INFORMATION: siRNA

<400> SEQUENCE: 5
uagcaaggcc aucuuggucu ucagg                                        25
```

```
<210> SEQ ID NO 6
<211> LENGTH: 25
<212> TYPE: RNA
<213> ORGANISM: Artificial Sequence
<220> FEATURE:
<223> OTHER INFORMATION: siRNA

<400> SEQUENCE: 6
ccugaagacc aagauggccu ugcua                                              25

<210> SEQ ID NO 7
<211> LENGTH: 25
<212> TYPE: RNA
<213> ORGANISM: Artificial Sequence
<220> FEATURE:
<223> OTHER INFORMATION: siRNA

<400> SEQUENCE: 7
cccuuggacu auguuagcau guaca                                              25

<210> SEQ ID NO 8
<211> LENGTH: 25
<212> TYPE: RNA
<213> ORGANISM: Artificial Sequence
<220> FEATURE:
<223> OTHER INFORMATION: siRNA

<400> SEQUENCE: 8
uguacaugcu aacauagucc aaggg                                              25

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
acatcagcgc tttgaccag                                                     19

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
taaaggtcgg atgaggat                                                      18

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
catcccacac aaggctaaca                                                    20

<210> SEQ ID NO 12
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 12
cagtgcccag agattgatga                                                 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
tctgggctta tgcatttgtg                                                 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
acaggagcac agtgatgtgg                                                 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tagagggagc cagagagacg                                                 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ttggcccaga actcctgtag                                                 20

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
ggaagacacc ccaatctcg                                                  19

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
catggcccca caattgac                                                   18
```

```
<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
cagggaagag agcagactga c                                              21

<210> SEQ ID NO 20
<211> LENGTH: 18
<212> TYPE: DNA
<213> ORGANISM: Artificial Sequence
<220> FEATURE:
<223> OTHER INFORMATION: Primer

<400> SEQUENCE: 20
cgctgctgca agaggact                                                  18

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
actttctcca caccctgctg                                                20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ggctgcgagg ctaaagagtc                                                20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ctggcttgat tgttcacgag                                                20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cagccctcat gctcacagac                                                20

<210> SEQ ID NO 25
<211> LENGTH: 21
<212> TYPE: DNA
<213> ORGANISM: Artificial Sequence
<220> FEATURE:
<223> OTHER INFORMATION: Primer
```

<400> SEQUENCE: 25
tggacaaagt attccgacca g                                              21

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
aggcctccaa taggttctg                                                 19

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
gctcaccccc aactacaatc                                                20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gcggccctca tagtgtaaag                                                20

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
acagaaatag ttacctgtgc aacact                                         26

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
gacttgctca taggacacac ca                                             22

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
cgtacggcaa tggctttatc                                                20

```
<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tcatctggat ggttgctctg                                               20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
atggaagacc actcgcattc                                               20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gctttatccc cacagactcg                                               20

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
gcaagctcgt gctctggt                                                 18

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gggcatgtag acagcacaca                                               20

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
aagcgctacc ggtcttctat c                                             21

<210> SEQ ID NO 38
<211> LENGTH: 20
<212> TYPE: DNA
<213> ORGANISM: Artificial Sequence
<220> FEATURE:
<223> OTHER INFORMATION: Primer
```

<400> SEQUENCE: 38
tgtgcacttc gtagggtcag                                              20

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
tctcccttgg ggctttac                                                18

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
tcccaacttc acctctcctg                                              20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
ttgggcatac tcaacaacca                                              20

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42
acttcgtccc cgttctcc                                                18

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
cttccagtca gagaacacct                                              20

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
ttgggctgaa tgtaactc                                                18

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
tggatgctct tcagttcgtg                                                    20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gcaacactca tcccacaatgc                                                   20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
ctgccaaact gcaacaagaa                                                    20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48 tccatgggtaga cacaccag                                                    20

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
cggggccccc tggaacatc                                                     19

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
ggtattgggg ttcacacacc                                                    20

<210> SEQ ID NO 51
<211> LENGTH: 20
<212> TYPE: DNA
<213> ORGANISM: Artificial Sequence
<220> FEATURE:
<223> OTHER INFORMATION: Primer

```
<400> SEQUENCE: 51
aatgtgctga gtcccagagg                                              20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
ggagcatcta ctggctctgc                                              20

<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53
cctcctttac ggtggacaaa c                                            21

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
atcaactcct cctgccaatg                                              20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
cttctcccac aagttcatgc                                              20

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
cgatgtcatt gttctggtag tcg                                          23
```